(12) United States Patent
Thrasher, III

(10) Patent No.: US 10,420,574 B2
(45) Date of Patent: Sep. 24, 2019

(54) DOUBLE FORCEPS

(71) Applicant: Richard Devere Thrasher, III, Mckinney, TX (US)

(72) Inventor: Richard Devere Thrasher, III, Mckinney, TX (US)

( * ) Notice: Subject to any disclaimer, the term of this patent is extended or adjusted under 35 U.S.C. 154(b) by 229 days.

(21) Appl. No.: 15/269,528

(22) Filed: Sep. 19, 2016

(65) Prior Publication Data

US 2018/0078271 A1 Mar. 22, 2018

(51) Int. Cl.
*A61B 17/28* (2006.01)
*B25B 7/02* (2006.01)
*A61B 17/00* (2006.01)

(52) U.S. Cl.
CPC ............ *A61B 17/282* (2013.01); *B25B 7/02* (2013.01); *A61B 2017/00353* (2013.01); *A61B 2017/2825* (2013.01); *A61B 2017/2829* (2013.01)

(58) Field of Classification Search
CPC ......... B26B 13/00; B26B 13/06; B26B 13/08; B26B 13/10; B26B 13/28; B26B 17/00; B26B 17/006; B26B 17/003; A61B 17/3201; A61B 17/28; A61B 17/2812; A61B 17/2816; A61B 17/282; A61B 2017/2825; A61B 2017/2829; A61B 17/29; A61B 2017/2926; A61B 2017/2939; A61B 2017/2945; A61B 2017/2947; A61B 17/30; A61B 2017/303
See application file for complete search history.

(56) References Cited

U.S. PATENT DOCUMENTS

| | | | | |
|---|---|---|---|---|
| 4,521,964 A | * | 6/1985 | Maruyama | A47G 21/06 30/145 |
| 6,457,238 B1 | * | 10/2002 | Maier | A47G 21/08 294/50.8 |
| 2008/0287985 A1 | * | 11/2008 | Patterson | A61B 17/2833 606/208 |

* cited by examiner

*Primary Examiner* — Wade Miles
(74) *Attorney, Agent, or Firm* — Goodhue, Coleman & Owens, P.C.

(57) ABSTRACT

Handheld forceps having plural pincers for grasping and holding multiple objects, such as Peanut or Cotton Kittner sponges, at the same time are disclosed. The handheld forceps include opposing arms having proximal and distal ends. A hinge connects the opposing arms together between the proximal and distal ends. The opposing arms articulate relative to each other about the hinge. A handle portion at the proximal ends of the opposing arms has an open and closed position for articulating the distal ends open and closed. Distal ends are configured with plural pincers whereby jaws are formed between the plural pincers for grasping and holding multiple objects at the same time.

19 Claims, 15 Drawing Sheets

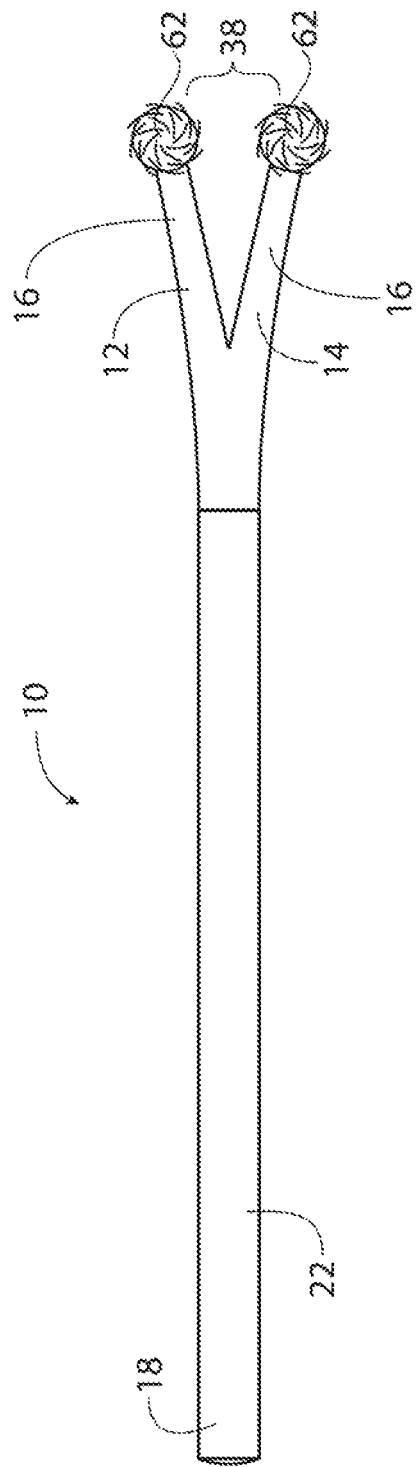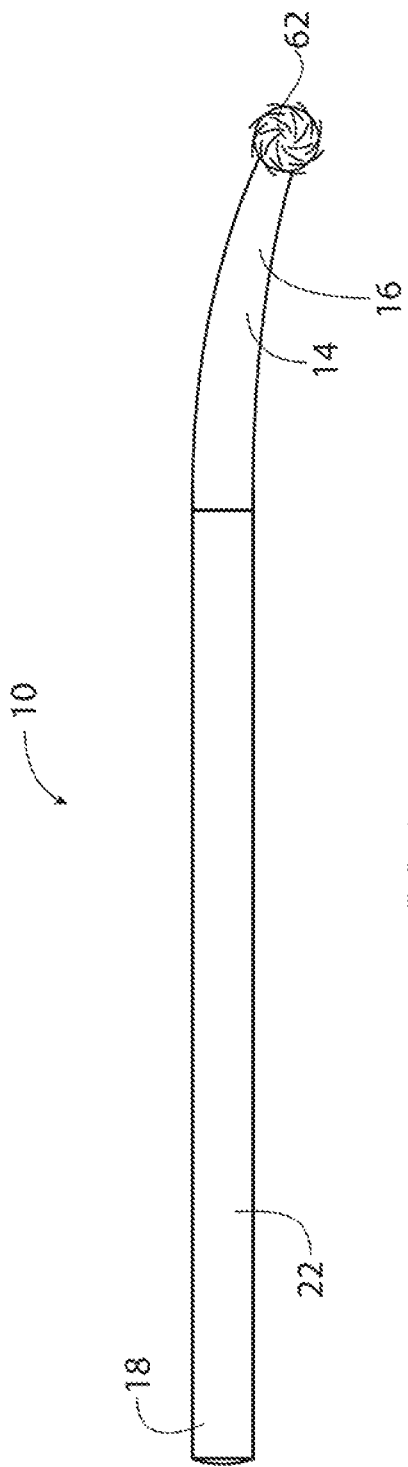

DOUBLE FORCEPS

BACKGROUND

I. Field of the Disclosure

Handheld forceps for grasping and holding objects are disclosed. More specifically, but not exclusively, handheld forceps having plural pincers and jaws for grasping and holding multiple small objects, such as cotton peanut sponges, cotton kittners or any like fibrous sponges/swabs, at the same time in a particular spaced apart arrangement are disclosed.

II. Description of the Prior Art

Handheld forceps are employed in various fields and endeavors, and with particular regularity in numerous medical fields and practices. Typically the devices are handheld and hinged whereby arm-actuated movement of a pair of pincers allows the operator to grasp and hold a single object. In some instances multiple objects may be secured at the same time by a pair of pincers, but typically not without some difficulty and certainly not in a particular spaced apart arrangement. Complexities and problems arise particularly when certain size, shape, and/or number of objects need held in a particular manner, distance apart and at the same time. In use, such as during a medical procedure, current handheld forceps offer little assistance in manipulating prolapsed tissue as they only are capable of securing a single Peanut or Cotton Kittner. Use of a single fibrous swab or other fibrous object for pushing and retracting tissue during a procedure does not create enough tissue separation to prevent tissue from prolapsing while still providing a space through which the medical professional can see. Moreover, the metal pincers of existing handheld forceps can damage tissue and nerves, are slippery and do not address these and other issues in the art.

SUMMARY

The present disclosure provides handheld forceps for grasping and simultaneously holding multiple objects. The handheld forceps include opposing arms having proximal and distal ends. A hinge connects the opposing arms together between the proximal and distal ends. The opposing arms articulate relative to each other about the hinge. A handle portion at the proximal ends of the opposing arms has an open and closed position for articulating the distal ends open and closed. In a preferred aspect, there are at least two pincers at the distal end of each of the opposing arms and a jaw formed between one pincer of one of the opposing arms and another pincer of the other one of the opposing arms.

In another aspect, a handheld medical tool is disclosed. The handheld medical tool includes opposing arms having proximal and distal ends. A hinge connects the opposing arms together between the proximal and distal ends. The opposing arms articulate relative to each other about the hinge. A handle portion at the proximal ends of the opposing arms has an open and closed position for articulating the distal ends open and closed. In a preferred aspect, there is a pincer at the distal end of each opposing arm and a pair of pincers disposed between the pincers on each opposing arm.

In another aspect, a handheld medical instrument is disclosed. The handheld medical instrument includes opposing arms having proximal and distal ends. A hinge connects the opposing arms together between the proximal and distal ends. The opposing arms articulate relative to each other about the hinge. A handle portion at the proximal ends of the opposing arms has an open and closed position for articulating the distal ends open and closed. In a preferred aspect, there is a pair of pincers at each of the distal ends of the opposing arms and a pair of jaws comprising one pincer from the pair of pincers for each of the opposing arms.

BRIEF DESCRIPTION OF THE DRAWINGS

Illustrated embodiments of the disclosure are described in detail below with reference to the attached drawing figures, which are incorporated by reference herein, and where:

FIG. 22 is a top view of other forceps shown in a condition of use in accordance with an illustrative embodiment; and FIG. 23 is a side view of the forceps of FIG. 20 shown in a condition of use in accordance with an illustrative embodiment.

DETAILED DESCRIPTION

Figure 1:
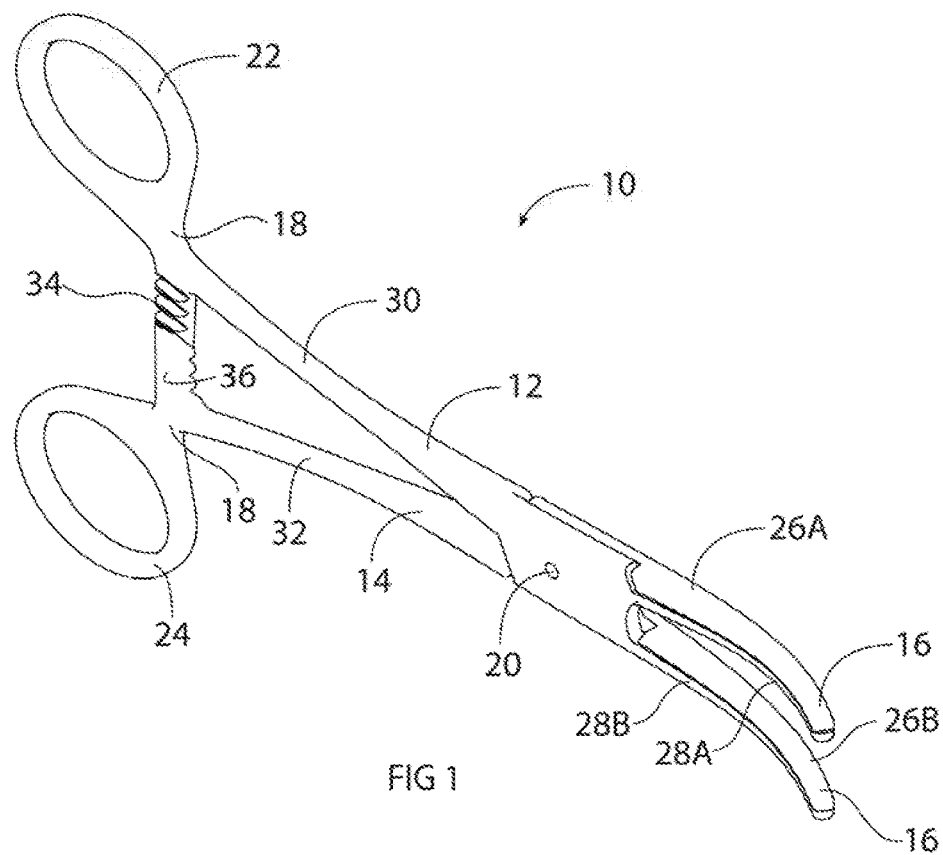
FIG. 1 is a perspective view of forceps shown in a closed position in accordance with an illustrative embodiment.
Figure 2:
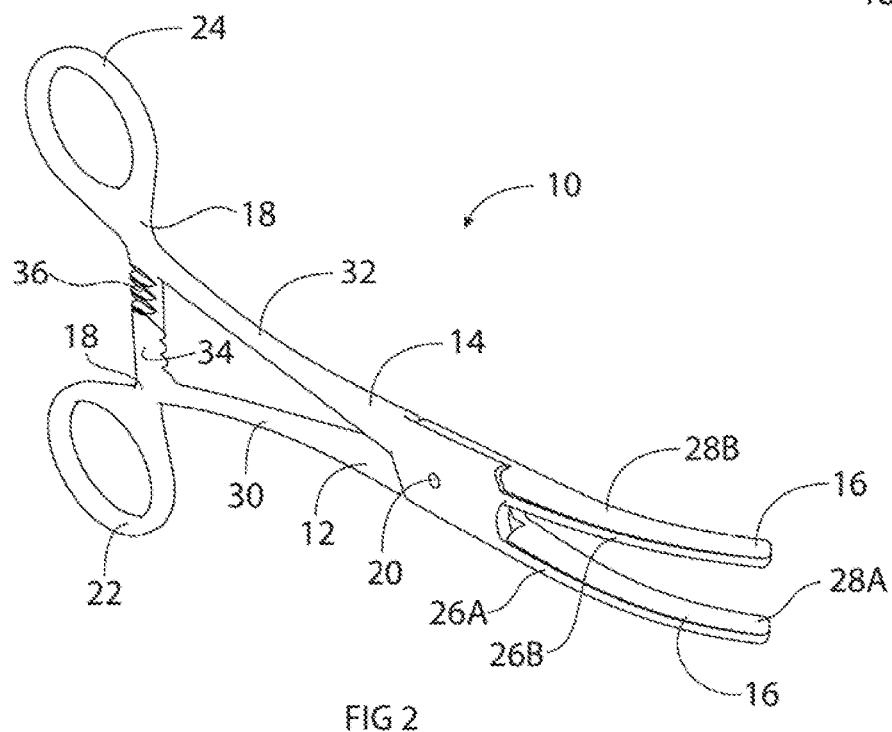
FIG. 2 is a perspective view showing the opposite side of the forceps shown in FIG. 1.

Handheld forceps for grasping and holding objects are disclosed in FIGS. 1-23. More specifically, but not exclusively, handheld forceps having plural pincers and jaws for grasping and holding multiple objects at the same time in a particulate space arrangement are also disclosed in FIGS. 1-23.

FIGS. 1-10 disclose forceps in accordance with at least one illustrative aspect of the present disclosure. The forceps 10 pictorially represented in FIGS. 1-10 include opposing arms 12, 14 that each extend generally between a distal end 16 and a proximal end 18 of the tool body or forceps 10. Pincers 28A, 28B are disposed at the distal end 16 of arm 12. Similarly, pincers 26A, 26B are disposed at the distal end of arm 14. In at least one preferred aspect of the present disclosure, pincers 26A, 26B, 28A, 28B are angled in an outwardly direction out of planarity with the tool body of the forceps 10. Handle portions 22, 24 are disposed on each arm 12, 14 at the proximal end 18. Arms 12, 14 include respective hinge points 46, 48 disposed between the pincers and respective shank portions 30, 32. The shank portion 30, 32 is disposed between respective handle portions 22, 24 and hinge points 46, 48. The shank portions 30, 32 can be lengthened or shortened to accommodate a desired tool body length. Arms 12, 14 are joined by a hinge 20 at respective hinge points 46, 48. The shank portions 30, 32 can also be altered (e.g., lengthened) to offer more leverage at hinge points 46, 48. The opposing arms 12, 14 articulate about hinge 20 by manipulation of the handle portions 22, 24. A locking member 34 is disposed adjacent the handle portion 22. Another locking member 36, opposing locking member 34, is disposed adjacent handle portion 24. The opposing locking members 34, 36 can be disposed anywhere along respective shank portions 30, 32 between the hinge 20 and respective proximal ends 18 of arms 12, 14. In a preferred aspect, locking member 34, 36 are disposed adjacent handle portions 22, 24. Each locking member 34, 36 includes respective teeth portions 35, 37 for removably fixing locking member 34, 36 together. Other securing means such as ribs, latches, hooks, loops, pins, and slides can removably secure locking member 34, 36 together. Other locking or securing means can be configured into hinge 20 to lock movement of arms 12, 14.

Figure 3:
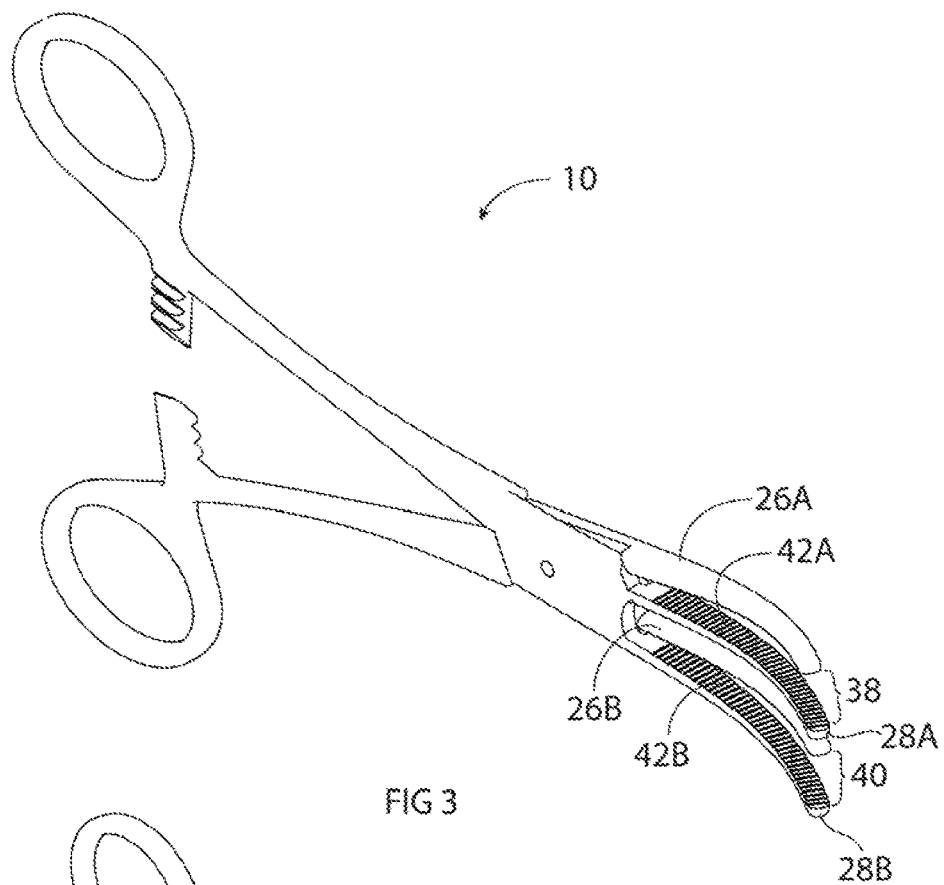
FIG. 3 is a perspective view of the forceps of FIG. 1 shown in an open position in accordance with an illustrative embodiment.
Figure 4:
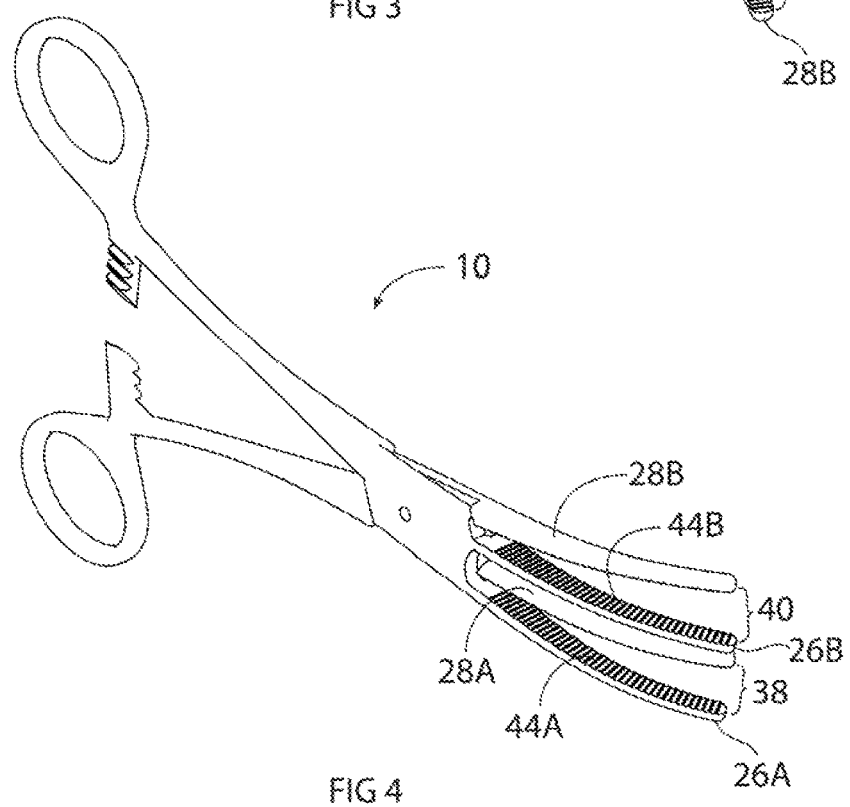
FIG. 4 is a perspective view of the forceps of FIG. 2 shown in an open position in accordance with an illustrative embodiment.

As shown pictorially in FIGS. 3-4, arms 12, 14 are articulated apart about hinge 20 to open or otherwise simultaneously separate pincer 26A from 28A and pincer 28A from 28B to form respective open jaws 38, 40. Conversely, when arms 12, 14 are articulated together about hinge 20, respective jaws 38, 40 close as pincers 26A, 28A and pincers 28A, 28B come together.

Figure 5:
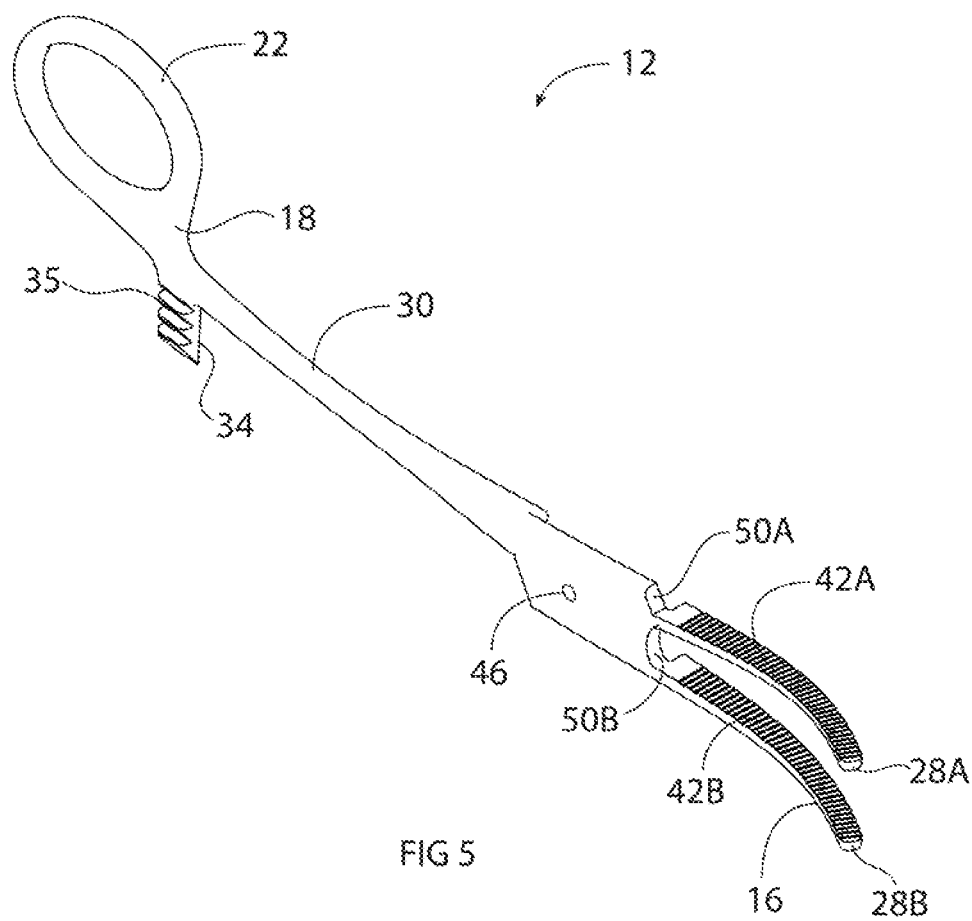
FIG. 5 is a perspective view of a left side portion of the forceps shown in FIG. 1 in accordance with an illustrative embodiment.
Figure 6:
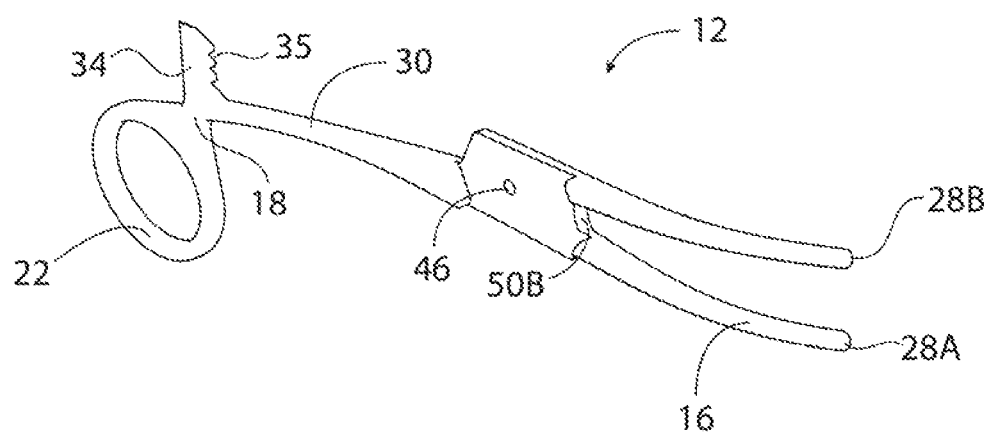
FIG. 6 is a perspective view showing the opposite side of the left side portion shown in FIG. 5.

As shown pictorially in FIGS. 5-6, arm 12 includes a pair of pincers 28A, 28B. Pincers 28A, 28B are attached to hinge point 46 and spaced apart by an offset portions 50A, 50B. Pincers 28A, 28B can include grips 42A, 42B. Grips 42A, 42B can be configured from one or more protuberations, undulations, or irregularities in the material comprising the gripping surface. Grips 42A, 42B can be fashioned into the gripping surface of pincers 28A. 28B by making alterations to the surface of the material forming the pincers 28A, 28B. In a preferred aspect of the present disclosure, arm 12 is manufactured from a medical-grade alloy, such as surgical stainless steel. In another aspect, grips 42A, 42B are formed from a separate layer of material fashioned atop the gripping surface of pincers 28A, 28B. For example, any type of hydrophobic, surgical grade rubber, plastic or silicone could be fashioned as grips 42A. 42B atop the gripping surface of pincers 28A, 28B. In at least one configuration of arm 12, pincers 28A, 28B are spaced apart in a generally parallel orientation relative to each another. In another configuration, pincers 28A, 28B are angled, to a small degree, away or toward each other. The offset portions 50A, 50B can include a mechanism (not shown) to control the degree of offset between pincers 28A, 28B. For example, one or both pincers 28A, 28B can be hingably mounted at offset portions 50A, 50B with the degree of separation between them controlled by an adjustment screw or other incremental adjustment mechanism. Adjustments can result in the distal end of pincers 28A, 28B being spaced closer together or further apart, either by increased or decreased angled or parallel separation, thereby increasing or decreasing the size of jaws 38, 40 (best illustrated in FIGS. 3-4). The portion of pincers 28A, 28B attached to offset portions 50A, 50B can also, by actuation of an adjustment mechanism, such as an adjustment screw, be spaced closer together or further apart. Such adjustments can provide, for example, a greater jaw 38, 40 opening.

Figure 7:
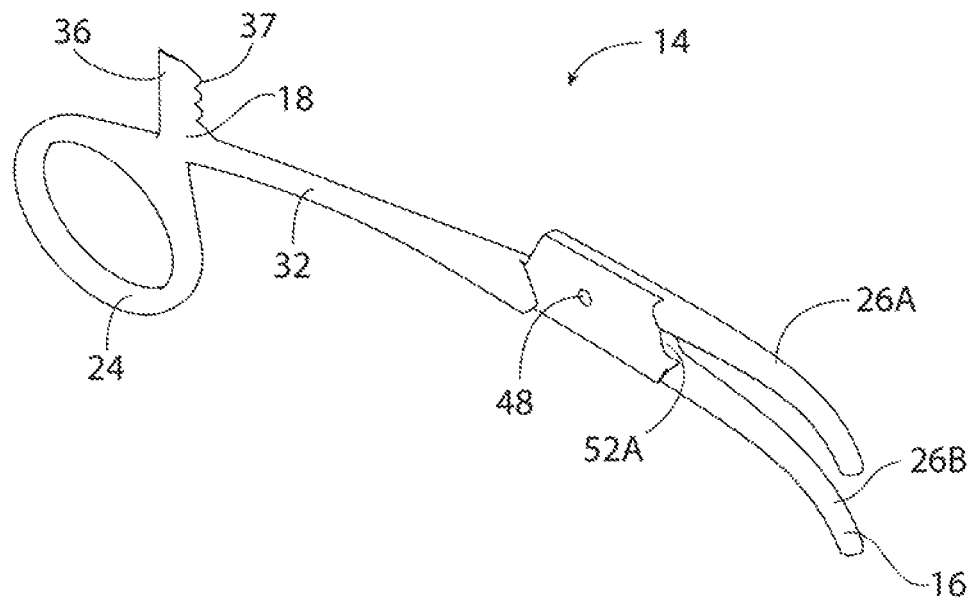
FIG. 7 is a perspective view of a right side portion of the forceps shown in FIG. 1 in accordance with an illustrative embodiment.
Figure 8:
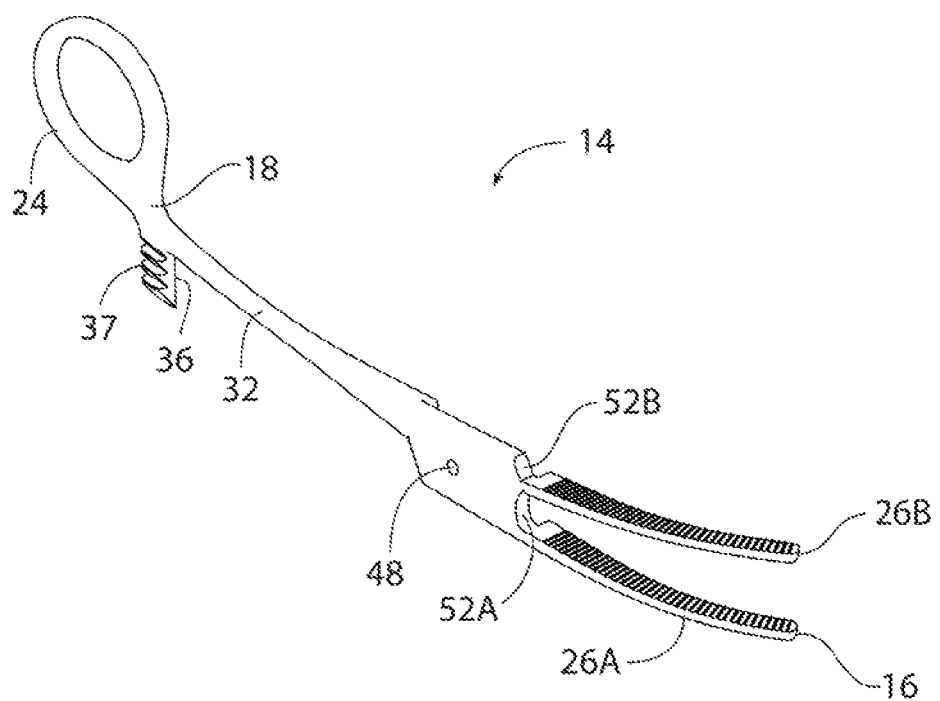
FIG. 8 is a perspective view showing the opposite side of the right side portion shown in FIG. 7.

As shown pictorially in FIGS. 7-8, arm 14 includes a pair of pincers 26A, 26B. Pincers 26A, 26B are attached to hinge point 48 and spaced apart by an offset portions 52A, 52B. Pincers 26A, 26B can include grips 44A, 44B, as shown in FIG. 4. Grips 44A, 44B can be configured from one or more protuberations, undulations, or irregularities in the material comprising the gripping surface. Grips 44A, 44B can be fashioned into the gripping surface of pincers 26A, 26B by making alterations to the surface of the material forming the pincers 26A, 26B. In a preferred aspect of the present disclosure, arm 14 is manufactured from a medical-grade alloy, such as surgical stainless steel. In another aspect, grips 44A, 44B are formed from a separate layer of material fashioned atop the gripping surface of pincers 26A, 26B. For example, any type of hydrophobic, surgical grade rubber, plastic or silicone could be fashioned as grips 44A, 44B atop the gripping surface of pincers 26A, 26B. In at least one configuration of arm 14, pincers 26A, 26B are spaced apart in a generally parallel orientation relative to each another. In another configuration, pincers 26A, 26B are angled, to a small degree, away or toward each other. The offset portions 52A, 52B can include a mechanism (not shown) to control the degree of offset between pincers 26A, 26B. For example, one or both pincers 26A, 26B can be hingably mounted at the offset portions 52A, 52B with the degree of separation between them controlled by an adjustment screw or other incremental adjustment mechanism. Adjustments can result in the distal end of pincers 26A, 26B being spaced closer together or further apart, either by increased or decreased angled or parallel separation, thereby increasing or decreasing the size of jaws 38, 40 (best illustrated in FIGS. 3-4). The portion of pincers 26A, 26B attached to respective offset portions 52A, 52B can also, by actuation of an adjustment mechanism, such as an adjustment screw, be spaced closer together or further apart. Such adjustments can provide, for example, a greater jaw 38, 40 opening.

Figure 9:
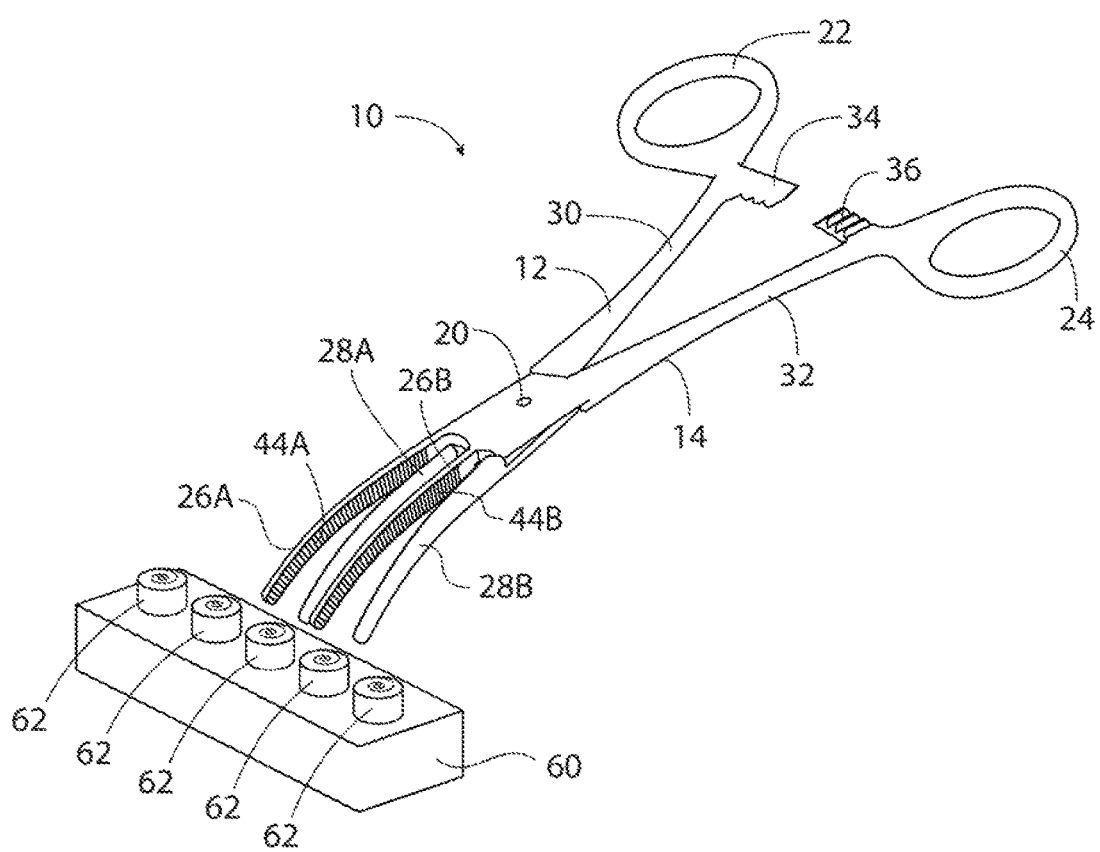
FIG. 9 is a perspective view of the forceps of FIG. 1 shown in a condition of use in accordance with an illustrative embodiment.
Figure 10:
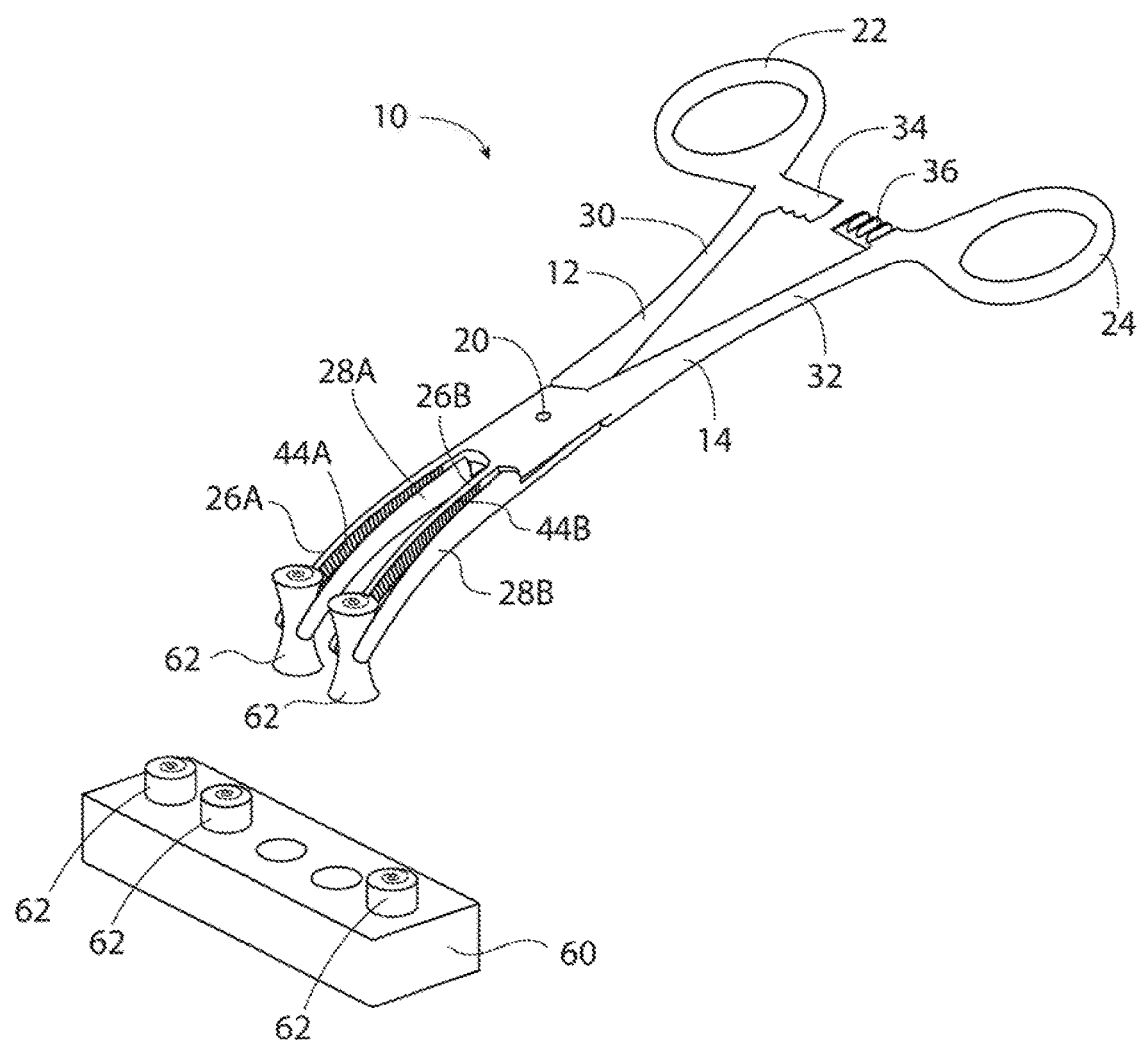
FIG. 10 is a perspective view of the forceps of FIG. 1 shown in a condition of use in accordance with another illustrative embodiment.
Figure 11:
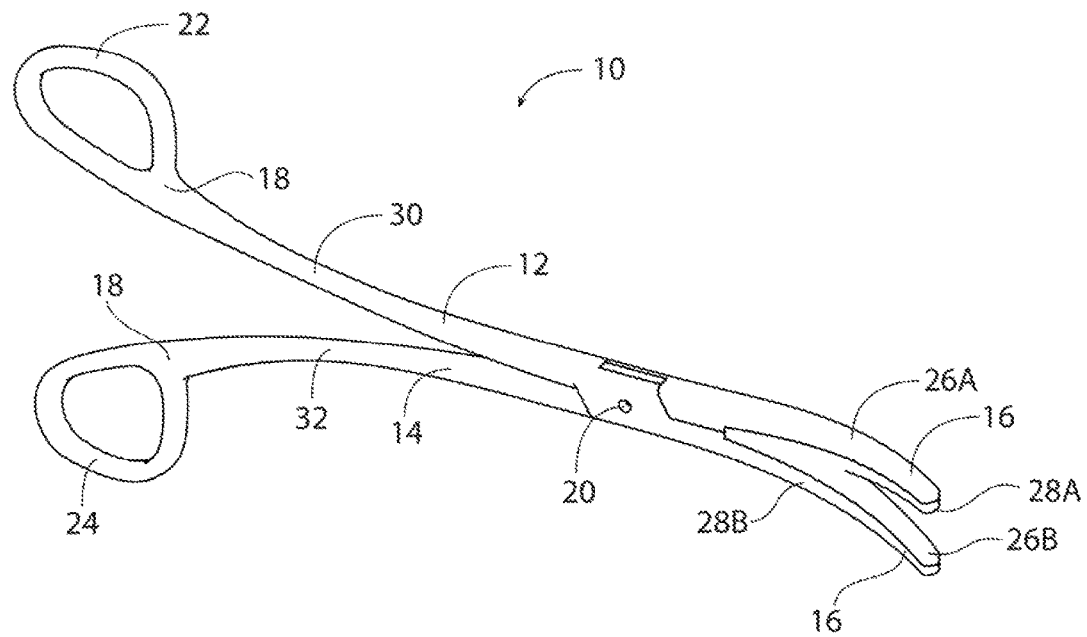
FIG. 11 is a perspective view of other forceps shown in a closed position in accordance with an illustrative embodiment.
Figure 12:
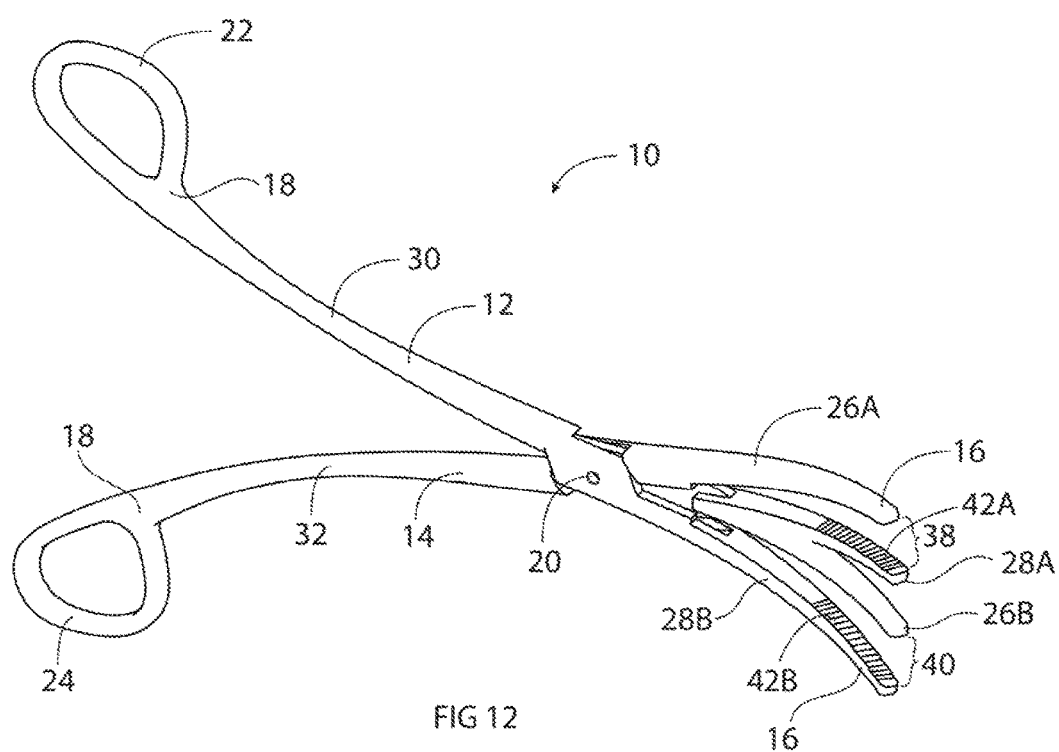
FIG. 12 is a perspective view of the forceps of FIG. 11 shown in an open position in accordance with an illustrative embodiment.

FIGS. 9-10 provide perspective views of in-use illustrations for the forceps 10. As discussed above, the pincers 26A, 26B, 28A, 28B have an arcuate shape bending generally outwardly from planarity with the body of the forceps 10. The bend angle can be anywhere from 15-60 degrees, and preferably 30-45 degrees relative to the handles 22, 24 as illustrated pictorially in FIGS. 9-10. The bend angle allows manipulation of tissues, nerves, fluids, and other possible vision-occluders to the extent that would not otherwise be possible with straight pincers or pincers with a zero degree bend. Illustrated holding a plurality of fibrous swabs 62, such as a plurality of cotton peanut sponges, cotton kittners or any like fibrous sponges/swabs, is a swab pouch 60. Examples of various contemplated fibrous swabs 62 and sponge pouch 60 are commercially available for purchase from American Surgical Company. With the jaws 38, 40 of pincers 26A, 28A and 26B, 28B open, as pictorially illustrated in FIG. 9, at least a pair of fibrous swabs 62 can simultaneously be secured between respective pincers 26A, 28A and 26B, 28B as best illustrated FIG. 10. Articulating handles 22, 24 from an open position (see FIG. 9) toward a closed position (see FIG. 10) closes jaws 38, 40 thereby grasping the pair of fibrous swabs 62 as shown. Grips 42A, 44A and 42B, 44B aid in grasping and retaining a grasp on the fibrous swabs 62 during manipulation of tissue, nerves, fluids or other bodily substances during, for example, a surgical procedure. Locking members 34, 36 on respective handles 22, 24 aid in firmly securing the fibrous swabs 62 within respective jaws 38, 40. Handles 22, 24 are articulated toward a closed position (see FIGS. 1-2) to lock the fibrous swabs 62 within respective jaws 38, 40 of opposing pincers 26A, 28A and 26B, 28B. As discussed above, adjusting the dimension and/or angle of portions 50A, 50B, 52A, 52B can alter the space between the jaws 38, 40 holding the pair of fibrous swabs 62. For example, increasing the dimension/angle of portions 50A, 50B, 52A, 52B can increase the separation distance between opposing jaws 38, 40 and thereby the separation distance between the pair of fibrous swabs 62 grasped by the pair of opposing jaws 38, 40. Alterations or changes to the dimension and/or angle of pincers 26A, 28A and 26B, 28B can be accomplished as disclosed herein. It can be desirable to increase separation distance between the pair of opposing pincers 26A, 28A and 26B, 28B to increase, for example, the tissue separation during pushing and retracting tissue for creating enough tissue separation to prevent tissue from prolapsing while still providing a space through which the medical professional can see. Moreover, the bend angle of pincers 26A, 28A and 26B, 28B allows further pushing and retraction of tissues, such as further manipulation of prolapsing tissue.

FIGS. 11-14 disclose forceps 10 in accordance with another illustrative aspect of the present disclosure. The forceps 10 pictorially represented in FIGS. 11-14 include opposing arms 12, 14 that each extend generally between a distal end 16 and a proximal end 18 of the tool body or forceps 10. Pincer 28B is disposed at the distal end 16 of arm 12. Similarly, pincer 26A is disposed at the distal end of arm 14. In at least one preferred aspect of the present disclosure, pincers 26A, 28B are angled in an outwardly direction out of planarity with the tool body of the forceps 10. Handle portions 22, 24 are disposed on each arm 12, 14 at the proximal end 18. Arms 12, 14 include respective hinge points 46, 48 disposed between the pincers and respective shank portions 30, 32. The shank portion 30, 32 is disposed between respective handle portions 22, 24 and hinge points 46, 48. The shank portions 30, 32 can be lengthened or shortened to accommodate a desired tool body length. Arms 12, 14 are joined by a hinge 20 at respective hinge points 46, 48. The shank portions 30, 32 can also be altered (e.g., lengthened) to offer more leverage at hinge points 46, 48. The opposing arms 12, 14 articulate about hinge 20 by manipulation of the handle portions 22, 24. A locking member, similar to locking member 34 shown in FIGS. 1-10, can be disposed adjacent the handle portion 22. Another locking member 36, similar to locking member 34 shown in FIGS. 1-10, opposing locking member 34, can be disposed adjacent handle portion 24. Opposing locking members can be disposed anywhere along respective shank portions 30, 32 between the hinge 20 and respective proximal ends 18 of arms 12, 14. In a preferred aspect, locking members can be disposed adjacent handle portions 22, 24, similar to locking members 34, 36 shown in FIGS. 1-10. Each locking member can includes respective teeth portions, similar to teeth portions 35, 37 shown in FIGS. 1-10, for removably fixing the locking members together. Other securing means such as ribs, latches, hooks, loops, pins, and slides can removably secure locking members, similar to locking members 34, 36 shown in FIGS. 1-10, together. Other locking or securing means can be configured into hinge 20 to lock movement of arms 12, 14.

The forceps 10 pictorially represented in FIGS. 11-14 include arm 13 that extends generally between hinge 20 and distal end 16 of the tool body or forceps 10. Pincer 28A is disposed at the distal end 16 of arm 13. Similarly, pincer 26B is disposed at the distal end of arm 13. In at least one preferred aspect of the present disclosure, pincers 26B, 28A are angled in an outwardly direction out of planarity with the tool body of the forceps 10. Arm 13 is pivotally joined by hinge point 47 to each arm 12, 14 at hinge points 46, 48 disposed between the pincers and respective shank portions 30, 32. Pincers 26B, 28A are connected to hinge point 47 by shank 31. As shown pictorially in FIGS. 11-13, arms 12, 14 are articulated apart about hinge 20 to open or otherwise simultaneously separate pincer 26A from 28A and pincer 26B from 28B to form respective open jaws 38, 40. Conversely, when arms 12, 14 are articulated together about hinge 20, respective jaws 38, 40 close as pincers 26A, 28A and pincers 26B, 28B come together. Hinge 20, in a preferred form, is configured to bias pincers 26B, 28A away from respective pincers 28B, 26A when arms 12, 14 are articulated from a closed position (see FIG. 11) toward an open position (see FIG. 13). A biasing mechanism (not shown) can be configured from spring-loading or spring-assisting movement of pincers 26B, 28A away from respective pincers 28B, 26A for opening both jaws 38, 40 nearly simultaneously when arms 12, 14 are articulated from a closed position (see FIG. 11) toward an open position (see FIG. 13). A biasing mechanism can also be configured into hinge points 46, 47, 48 for biasing movement of pincers 26B. 28A away from respective pincers 28B, 26A for opening both jaws 38, 40 nearly simultaneously when arms 12, 14 are articulated from a closed position (see FIG. 11) toward an open position (see FIG. 13). In another aspect, a biasing mechanism such as surface etching configured at/on hinge points 46, 47, 48 and/or hinge 20 can bias movement of pincers 26B, 28A away from respective pincers 28B. 26A for opening both jaws 38, 40 nearly simultaneously when arms 12, 14 are articulated from a closed position (see FIG. 11) toward an open position (see FIG. 13). In at least one other aspect, hinge 20 may be configured whereby the hinge point 47 of arm 13 free-floats within hinge 20.

As shown pictorially in FIGS. 11-14, arms 12, 14 include respective pincers 28B, 26A. Pincers 28B, 26A are attached to and spaced away from a pair of respective planes collinear with respective hinge points 46, 48 by offset portions 50B, 50A. Pincers 28B, 26A can include grips 42B, 44A. Grips 42B, 44A can be configured from one or more protuberations, undulations, or irregularities in the material comprising the gripping surface. Grips 42B, 44A can be fashioned into the gripping surface of pincers 28B, 26A by making alterations to the surface of the material forming the pincers 28B, 26A. In a preferred aspect of the present disclosure, arms 12, 14 are manufactured from a medical-grade alloy, such as surgical stainless steel. In another aspect, grips 42B, 44A are formed from a separate layer of material fashioned atop the gripping surface of pincers 28B, 26A. For example, any type of hydrophobic, surgical grade rubber, plastic or silicone could be fashioned as grips 42B, 44A atop the gripping surface of pincers 28B, 26A. In at least one configuration of arm 12, pincers 28B, 26A are spaced apart in a generally parallel orientation relative to each another. In another configuration, pincers 28B, 26A are angled, to a small degree, away or toward each other. The offset portions 50B, 50A can include a mechanism (not shown) to control the degree of offset between pincers 28B, 26A. For example, one or both pincers 28B. 26A can be hingably mounted at offset portions 50B, 50A with the degree of separation between them controlled by an adjustment screw or other incremental adjustment mechanism. Adjustments can result in the distal end of pincers 28B, 26A being spaced closer together or further apart, either by increased or decreased angled or parallel separation, thereby increasing or decreasing the size of jaws 38, 40 (best illustrated in FIG. 13). The portion of pincers 28B, 26A attached to offset portions 50B, 50A can also, by actuation of an adjustment mechanism, such as an adjustment screw, be spaced closer together or further apart. Such adjustments can provide, for example, a greater jaw 38, 40 opening.

Figure 13:
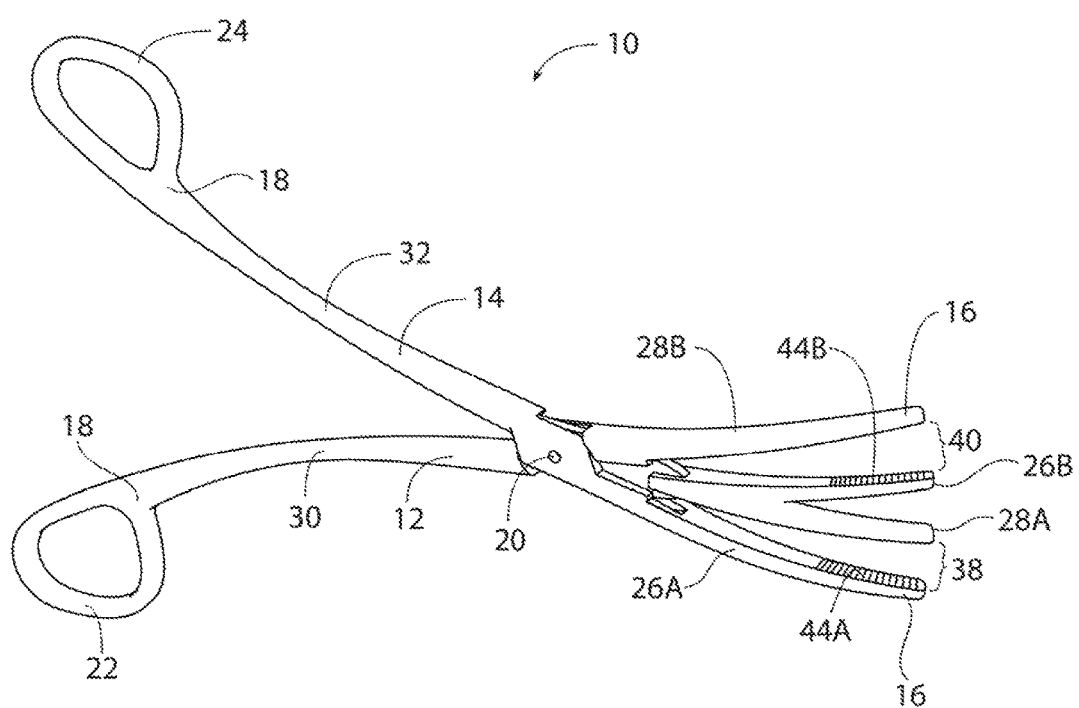
FIG. 13 is a perspective view showing the opposite side of the forceps shown in FIG. 12.
Figure 14:
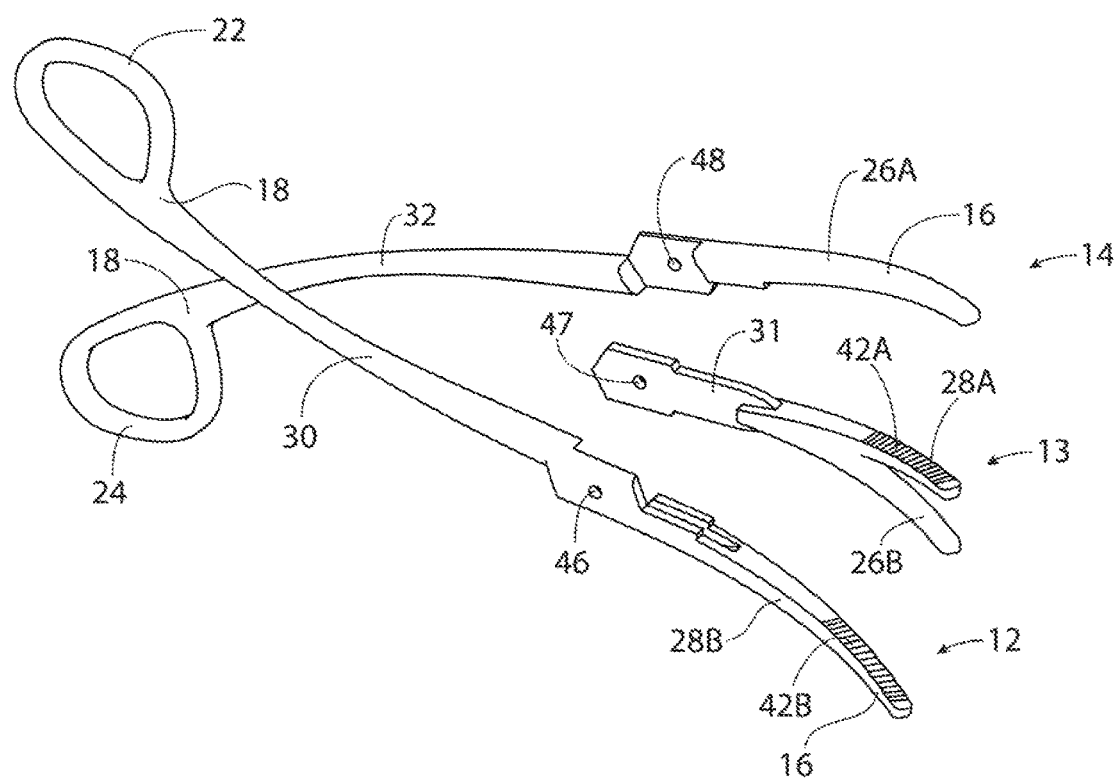
FIG. 14 is an exploded view of the forceps shown in FIG. 11.

As also shown pictorially in FIGS. 11-14, arm 13 includes a pair of pincers 28A, 26B. Pincers 28A, 26B are attached to hinge point 47 and spaced apart by an offset portion 51. The offset portion can be configured into the shank 31 or arm 13 and/or the portion of pincers 28A, 26B connecting pincers 28A, 26B to shank 31. Pincers 28A, 26B can include grips 42A, 44B, as shown in FIGS. 13-14. Grips 42A, 44B can be configured from one or more protuberations, undulations, or irregularities in the material comprising the gripping surface. Grips 42A, 44B can be fashioned into the gripping surface of pincers 28A, 26B by making alterations to the surface of the material forming the pincers 28A. 26B. In a preferred aspect of the present disclosure, arm 13 is manufactured from a medical-grade alloy, such as surgical stainless steel. In another aspect, grips 42A, 44B are formed from a separate layer of material fashioned atop the gripping surface of pincers 28A. 26B. For example, any type of hydrophobic, surgical grade rubber, plastic or silicone could be fashioned as grips 42A, 44B atop the gripping surface of pincers 28A, 26B. In at least one configuration of arm 13, pincers 28A, 26B are spaced apart in a generally parallel orientation relative to each another. In another configuration, pincers 26A, 26B are angled, to a small degree, away or toward each other. The offset portion 51 can include a mechanism (not shown) to control the degree of offset between pincers 28A, 26B and to conform to the degree of offset between pincers 28B, 26A, which is also changeable as contemplated and described above. For example, one or both pincers 28A, 26B can be hingably mounted at the offset portion 51 with the degree of separation between them controlled by an adjustment screw or other incremental adjustment mechanism. Adjustments can result in the distal end of pincers 28A, 26B being spaced closer together or further apart, either by increased or decreased angled or parallel separation (including like adjustments to pincers 28B, 26A), thereby increasing or decreasing the size of jaws 38, 40 (best illustrated in FIGS. 12-13). The portion of pincers 28A, 26B attached to offset portion 51 can also, by actuation of an adjustment mechanism, such as an adjustment screw, be spaced closer together or further apart. Such adjustments can provide, for example, a greater jaw 38, 40 opening.

As discussed above, the pincers 26A, 26B, 28A, 28B have an arcuate shape bending generally outwardly from planarity with the body of the forceps 10. The bend angle can be anywhere from 15-60 degrees, and preferably 30-45 degrees relative to the handles 22, 24 as illustrated pictorially in FIGS. 11-14. The bend angle allows manipulation of tissues, nerves, fluids, and other possible vision-occluders to the extent that would not otherwise be possible with straight pincers or pincers with a zero degree bend. Jaws 38, 40 are configured to hold at least a pair of fibrous swabs (e.g., fibrous swabs 62 shown in FIGS. 9-10), such as a plurality of cotton peanut sponges, cotton kittners or any like fibrous sponges/swabs. Examples of various contemplated fibrous swabs and sponge pouch (e.g., see sponge pouch 60 in FIGS. 9-10) are commercially available for purchase from American Surgical Company. With the jaws 38, 40 of pincers 26A, 28A and 26B, 28B open, as pictorially illustrated in FIGS. 12-13, at least a pair of fibrous swabs can simultaneously be secured between respective pincers 26A, 28A and 26B. 28B in a way similarly shown in FIG. 10. Articulating handles 22, 24 from an open position (see FIGS. 12-13) toward a closed position (see FIG. 11) closes jaws 38, 40 thereby grasping the pair of fibrous swabs in a way similarly shown in FIGS. 9-10. Grips 42A, 44A and 42B, 44B aid in grasping and retaining a grasp on the fibrous swabs during manipulation of tissue, nerves, fluids or other bodily substances during, for example, a surgical procedure. Locking members, such as similar ones 34, 36 shown in FIGS. 1-10, can be configured on respective handles 22, 24 and aid in firmly securing fibrous swabs within respective jaws 38, 40. Handles 22, 24 are articulated toward a closed position (see FIG. 11) to lock the fibrous swabs within respective jaws 38, 40 of opposing pincers 26A, 28A and 26B, 28B in a way similarly shown in FIGS. 9-10. As discussed above, adjusting the dimension and/or angle of portions 50B, 50A, 51 can alter the space between the jaws 38, 40 holding the pair of fibrous swabs. For example, increasing the dimension/angle of portions SOB, 50A, 51 can increase the separation distance between opposing jaws 38, 40 and thereby the separation distance between the pair of fibrous swabs grasped by the pair of opposing jaws 38, 40. Alterations or changes to the dimension and/or angle of pincers 26A, 28A and 26B, 28B can be accomplished as disclosed herein. It can be desirable to increase separation distance between the pair of opposing pincers 26A, 28A and 26B, 28B to increase, for example, the tissue separation during pushing and retracting tissue for creating enough tissue separation to prevent tissue from prolapsing while still providing a space through which the medical professional can see. Moreover, the bend angle of pincers 26A, 28A and 26B, 28B allows further pushing and retraction of tissues, such as further manipulation of prolapsing tissue.

Figure 15:
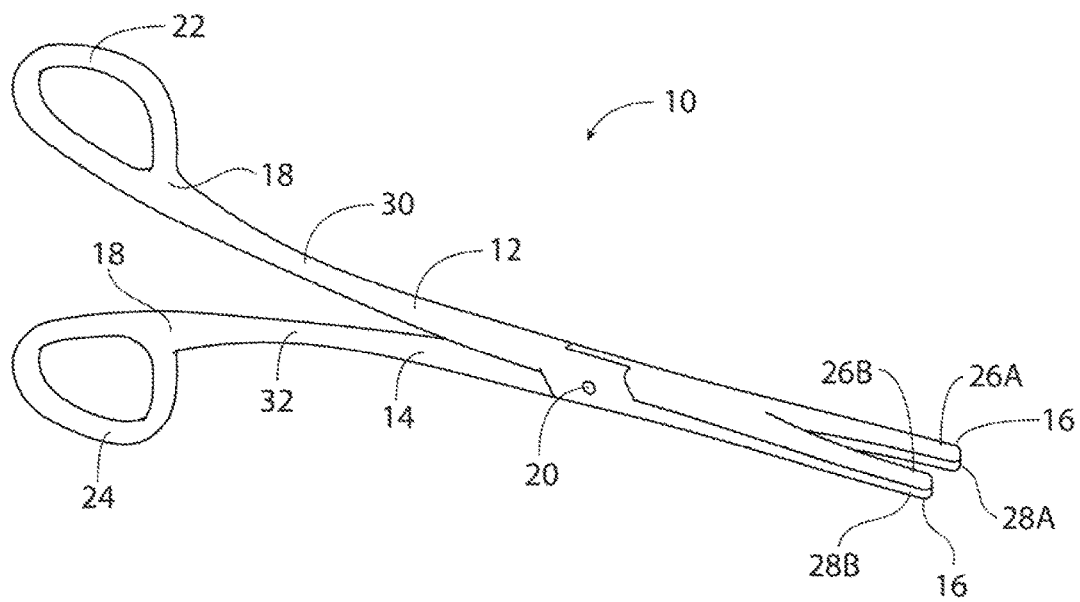
FIG. 15 is a perspective view of other forceps shown in a closed position in accordance with an illustrative embodiment.
Figure 16:
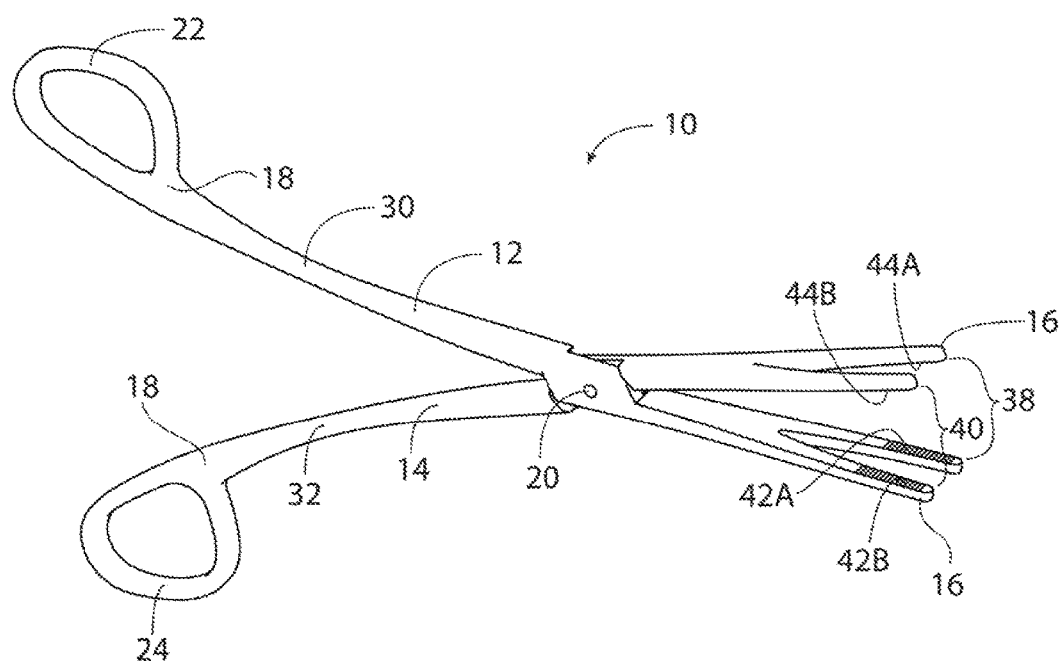
FIG. 16 is a perspective view of the forceps of FIG. 15 shown in an open position in accordance with an illustrative embodiment.

FIG. 15-16 disclose forceps in accordance with another illustrative aspect of the present disclosure. The forceps 10 pictorially represented in FIGS. 15-16 include opposing arms 12, 14 that each extend generally between a distal end 16 and a proximal end 18 of the tool body or forceps 10. Pincers 28A, 28B are disposed at the distal end 16 of arm 12.

Similarly, pincers 26A, 26B are disposed at the distal end of arm 14. In at least one preferred aspect of the present disclosure, pincers 26A, 26B, 28A, 28B can be angled in an upwardly or downwardly direction out of planarity with the tool body of the forceps 10. Handle portions 22, 24 are disposed on each arm 12, 14 at the proximal end 18. Arms 12, 14 include a hinge 20 of respective hinge points disposed between the pincers and respective shank portions 30, 32. The shank portion 30, 32 is disposed between respective handle portions 22, 24 and hinge 20. The shank portions 30, 32 can be lengthened or shortened to accommodate a desired tool body length. Arms 12, 14 are joined by a hinge 20 at respective hinge points. The shank portions 30, 32 can also be altered (e.g., lengthened) to offer more leverage at hinge 20. The opposing arms 12, 14 articulate about hinge 20 by manipulation of the handle portions 22, 24. A locking member fashioned in a way similarly shown in FIGS. 1-10 can be disposed adjacent the handle portion 22. Another locking member fashioned in a way similarly shown in FIGS. 1-10 can be configured opposing the other locking member and disposed adjacent handle portion 24. The opposing locking fashioned in a way similarly shown in FIGS. 1-10 can be disposed anywhere along respective shank portions 30, 32 between the hinge 20 and respective proximal ends 18 of arms 12, 14. In a preferred aspect, locking members fashioned in a way similarly shown in FIGS. 1-10 can be disposed adjacent handle portions 22, 24. Each locking member fashioned in a way similarly shown in FIGS. 1-10 can include respective teeth portions 35, 37 for removably fixing locking member together. Other securing means such as ribs, latches, hooks, loops, pins, and slides can removably secure locking member together. Other locking or securing means can be configured into hinge 20 to lock movement of arms 12, 14.

As shown pictorially in FIG. 16, arms 12, 14 are articulated apart about hinge 20 to open or otherwise simultaneously separate pincer 26A from 28A and pincer 28A from 28B to form respective open jaws 38, 40. Conversely, when arms 12, 14 are articulated together about hinge 20, respective jaws 38, 40 close as pincers 26A, 28A and pincers 28A, 28B come together as shown in FIG. 15.

As shown pictorially in FIG. 16, arm 12 includes a pair of pincers 28A, 28B. Pincers 28A, 28B are attached to hinge 20 and spaced apart by an offset portion 50A. Pincers 28A, 28B can include grips 42A, 42B. Grips 42A, 42B can be configured from one or more protuberations, undulations, or irregularities in the material comprising the gripping surface. Grips 42A, 42B can be fashioned into the gripping surface of pincers 28A, 28B by making alterations to the surface of the material forming the pincers 28A, 28B. In a preferred aspect of the present disclosure, arm 12 is manufactured from a medical-grade alloy, such as surgical stainless steel. In another aspect, grips 42A, 42B are formed from a separate layer of material fashioned atop the gripping surface of pincers 28A, 28B. For example, any type of hydrophobic, surgical grade rubber, plastic or silicone could be fashioned as grips 42A, 42B atop the gripping surface of pincers 28A, 28B. In at least one configuration of arm 12, pincers 28A, 28B are spaced apart in a generally parallel orientation relative to each another. In a preferred configuration, pincers 28A, 28B are angled away from each other. The offset portion 50A can include a mechanism (not shown) to control the degree of offset between pincers 28A, 28B. For example, one or both pincers 28A, 28B can be hingably mounted at offset portion 50A with the degree of separation between them controlled by an adjustment screw or other incremental adjustment mechanism. Adjustments can result in the distal end of pincers 28A, 28B being spaced closer together or further apart, thereby increasing or decreasing the separation distance between jaws 38, 40 (best illustrated in FIG. 16). The portion of pincers 28A, 28B attached to offset portion 50A can also, by actuation of an adjustment mechanism, such as an adjustment screw, be spaced closer together or further apart. Such adjustments can provide, for example, a greater jaw 38, 40 separation.

As shown pictorially in FIG. 16, arm 14 includes a pair of pincers 26A, 26B. Pincers 26A, 26B are attached to hinge 20 and spaced apart by an offset portion 52A. Pincers 26A, 26B can include grips 44A, 44B, as best shown in FIG. 16. Grips 44A, 44B can be configured from one or more protuberations, undulations, or irregularities in the material comprising the gripping surface. Grips 44A, 44B can be fashioned into the gripping surface of pincers 26A, 26B by making alterations to the surface of the material forming the pincers 26A, 26B. In a preferred aspect of the present disclosure, arm 14 is manufactured from a medical-grade alloy, such as surgical stainless steel. In another aspect, grips 44A, 44B are formed from a separate layer of material fashioned atop the gripping surface of pincers 26A, 26B. For example, any type of hydrophobic, surgical grade rubber, plastic or silicone could be fashioned as grips 44A, 44B atop the gripping surface of pincers 26A, 26B. In at least one configuration of arm 14, pincers 26A, 26B are spaced apart in a generally parallel orientation relative to each another. In a preferred configuration, pincers 26A, 26B are angled away from each other. The offset portion 52A can include a mechanism (not shown) to control the degree of offset between pincers 26A, 26B. For example, one or both pincers 26A, 26B can be hingably mounted at the offset portion 52A with the degree of separation between them controlled by an adjustment screw or other incremental adjustment mechanism. Adjustments can result in the distal end of pincers 26A, 26B being spaced closer together or further apart, thereby increasing or decreasing the separation distance between jaws 38, 40 (best illustrated in FIG. 16). The portion of pincers 26A, 26B attached to respective offset portion 52A can also, by actuation of an adjustment mechanism, such as an adjustment screw, be spaced closer together or further apart. Such adjustments can provide, for example, a greater jaw 38, 40 separation.

The pincers 26A, 26B, 28A, 28B are angled generally outwardly from planarity with the body of the forceps 10. The angle can be anywhere from 5-45 degrees, and preferably 10-25 degrees as illustrated pictorially in FIGS. 15-16. The separation between the distal end 16 of pincers 26A, 28A and 26B, 28B allows manipulation of tissues, nerves, fluids, and other possible vision-occluders to the extent that would not otherwise be possible with straight pincers or pincers with no separation between the distal end 16 of pincers 26A, 28A and 26B, 28B. Jaws 38, 40 are configured to hold at least a pair of fibrous swabs (e.g., fibrous swabs 62 shown in FIGS. 9-10), such as a plurality of cotton peanut sponges, cotton kittners or any like fibrous sponges/swabs. Examples of various contemplated fibrous swabs and sponge pouch (e.g., see sponge pouch 60 in FIGS. 9-10) are commercially available for purchase from American Surgical Company. With the jaws 38, 40 of pincers 26A, 28A and 26B, 28B open, as pictorially illustrated in FIG. 16, at least a pair of fibrous swabs can simultaneously be secured between respective pincers 26A, 28A and 26B, 28B in a way similarly shown in FIG. 10. Articulating handles 22, 24 from an open position (see FIG. 16) toward a closed position (see FIG. 5) closes jaws 38, 40 thereby grasping the pair of fibrous swabs in a way similarly shown in FIGS. 9-10. Grips 42A, 44A and 42B, 44B aid in grasping and retaining a grasp on the fibrous swabs during manipulation of tissue, nerves, fluids or other bodily substances during, for example, a surgical procedure. Locking members, such as similar ones 34, 36 shown in FIGS. 1-10, can be configured on respective handles 22, 24 and aid in firmly securing fibrous swabs within respective jaws 38, 40. Handles 22, 24 are articulated toward a closed position (see FIG. 15) to lock the fibrous swabs within respective jaws 38, 40 of opposing pincers 26A, 28A and 26B, 28B in a way similarly shown in FIGS. 9-10. As discussed above, adjusting the dimension and/or angle of offset portion 52A can alter the separation between the jaws 38, 40 holding the pair of fibrous swabs. For example, increasing the dimension/angle of portion 52A can increase the separation distance between opposing jaws 38, 40 and thereby the separation distance between the pair of fibrous swabs grasped by the pair of opposing jaws 38, 40. Alterations or changes to the dimension and/or angle of pincers 26A, 28A and 26B, 28B can be accomplished as disclosed herein. It can be desirable to increase separation distance between the pair of opposing pincers 26A, 28A and 26B, 28B to increase, for example, the tissue separation during pushing and retracting tissue for creating enough tissue separation to prevent tissue from prolapsing while still providing a space through which the medical professional can see. Moreover, the angle of separation between pincers 26A, 28A and 26B, 28B allows further pushing and retraction of tissues, such as further manipulation of prolapsing tissue.

Figure 17:
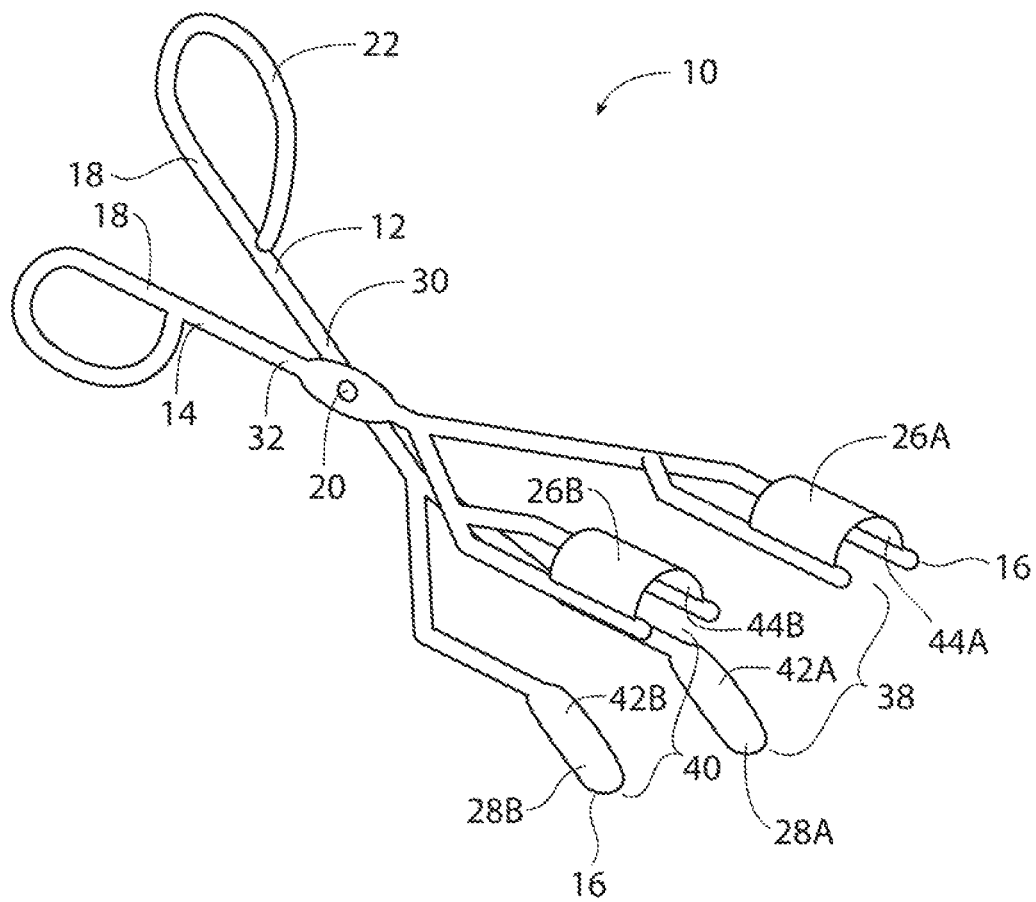
FIG. 17 is a perspective view of other forceps shown in an open position in accordance with an illustrative embodiment.
Figure 18:
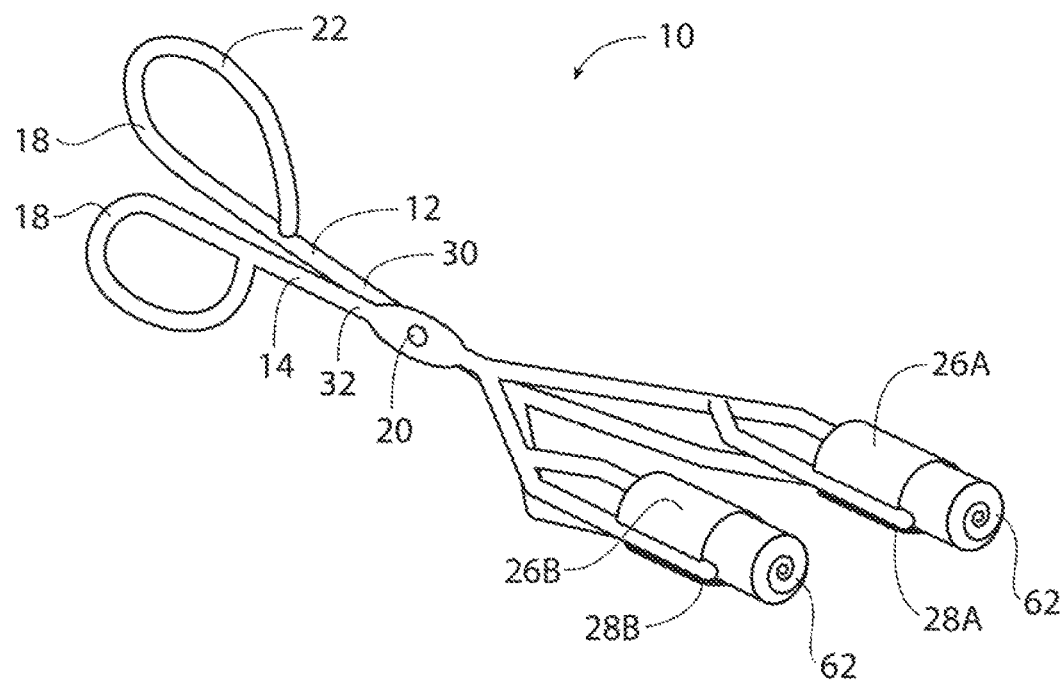
FIG. 18 is a perspective view of the forceps of FIG. 17 shown in a condition of use in accordance with an illustrative embodiment.
Figure 19:
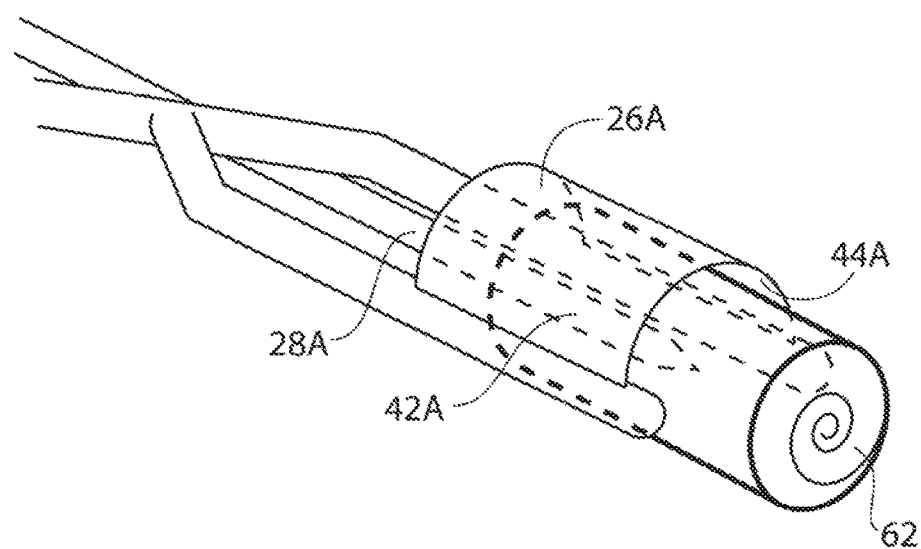
FIG. 19 is a perspective view of the forceps of FIG. 17 showing another configuration in accordance with an illustrative embodiment.

FIGS. 17-19 disclose forceps in accordance with another illustrative aspect of the present disclosure. The forceps 10 pictorially represented in FIGS. 17-19 include opposing arms 12, 14 that each extend generally between a distal end 16 and a proximal end 18 of the tool body or forceps 10. Pincers 28A, 28B are disposed at the distal end 16 of arm 12. Similarly, pincers 26A, 26B are disposed at the distal end of arm 14. In at least one preferred aspect of the present disclosure, pincers 26A, 26B and pincers 28A, 28B can be angled away from or toward each other. Handle portions 22, 24 are disposed on each arm 12, 14 at the proximal end 18. Arms 12, 14 include a hinge 20 of respective hinge points disposed between the pincers and respective shank portions 30, 32. The shank portion 30, 32 is disposed between respective handle portions 22, 24 and hinge 20. The shank portions 30, 32 can be lengthened or shortened to accommodate a desired tool body length. Arms 12, 14 are joined by a hinge 20 at respective hinge points. The shank portions 30, 32 can also be altered (e.g., lengthened) to offer more leverage at hinge 20. The opposing arms 12, 14 articulate about hinge 20 by manipulation of the handle portions 22, 24. A locking member fashioned in a way similarly shown in FIGS. 1-10 can be disposed adjacent the handle portion 22. Another locking member fashioned in a way similarly shown in FIGS. 1-10 can be configured opposing the other locking member and disposed adjacent handle portion 24. The opposing locking fashioned in a way similarly shown in FIGS. 1-10 can be disposed anywhere along respective shank portions 30, 32 between the hinge 20 and respective proximal ends 18 of arms 12, 14. In a preferred aspect, locking members fashioned in a way similarly shown in FIGS. 1-10 can be disposed adjacent handle portions 22, 24. Each locking member fashioned in a way similarly shown in FIGS. 1-10 can include respective teeth portions 35, 37 for removably fixing locking member together. Other securing means such as ribs, latches, hooks, loops, pins, and slides can removably secure locking member together. Other locking or securing means can be configured into hinge 20 to lock movement of arms 12, 14.

As shown pictorially in FIGS. 17-18, arms 12, 14 are articulated apart about hinge 20 to open or otherwise simultaneously separate pincer 26A from 28A and pincer 28A from 28B to form respective open jaws 38, 40. Conversely, when arms 12, 14 are articulated together about hinge 20, respective jaws 38, 40 close as pincers 26A, 28A and pincers 28A. 28B come together as shown in FIG. 18.

As shown pictorially in FIG. 17, arm 12 includes a pair of pincers 28A, 28B. Pincers 28A, 28B are attached to hinge 20 and spaced apart by an offset portion 52A. Pincers 28A, 28B can include grips 42A, 42B and are preferably contoured to receive a round fibrous swab, as best shown in FIGS. 17-19. Grips 42A, 42B can be configured from one or more protuberations, undulations, or irregularities in the material comprising the gripping surface. Grips 42A, 42B can be fashioned into the gripping surface of pincers 28A, 28B by making alterations to the surface of the material forming the pincers 28A, 28B. In a preferred aspect of the present disclosure, arm 12 is manufactured from a medical-grade alloy, such as surgical stainless steel. In another aspect, grips 42A, 42B are formed from a separate layer of material fashioned atop the gripping surface of pincers 28A, 28B. For example, any type of hydrophobic, surgical grade rubber, plastic or silicone could be fashioned as grips 42A, 42B atop the gripping surface of pincers 28A, 28B. In at least one configuration of arm 12, pincers 28A, 28B are spaced apart in a generally parallel orientation relative to each another. In a preferred configuration, pincers 28A, 28B are angled away from each other. The offset portion 52A can include a mechanism (not shown) to control the degree of offset between pincers 28A, 28B. For example, one or both pincers 28A, 28B can be hingably mounted at offset portion 52A with the degree of separation between them controlled by an adjustment screw or other incremental adjustment mechanism. Adjustments can result in the distal end of pincers 28A, 28B being spaced closer together or further apart, thereby increasing or decreasing the separation distance between jaws 38, 40 (best illustrated in FIGS. 17-18). The portion of pincers 28A, 28B attached to offset portion 52A can also, by actuation of an adjustment mechanism, such as an adjustment screw, be spaced closer together or further apart. Such adjustments can provide, for example, a greater distance between jaws 38, 40

As shown pictorially in FIG. 17, arm 14 includes a pair of pincers 26A, 26B. Pincers 26A, 26B are attached to hinge 20 and spaced apart by an offset portion 52A. Pincers 26A, 26B can include grips 44A, 44B and are preferably contoured to receive a round fibrous swab, as best shown in FIGS. 17-19. Grips 44A, 44B can be configured from one or more protuberations, undulations, or irregularities in the material comprising the gripping surface. Grips 44A, 44B can be fashioned into the gripping surface of pincers 26A, 26B by making alterations to the surface of the material forming the pincers 26A, 26B. In a preferred aspect of the present disclosure, arm 14 is manufactured from a medical-grade alloy, such as surgical stainless steel. In another aspect, grips 44A, 44B are formed from a separate layer of material fashioned atop the gripping surface of pincers 26A, 26B. For example, any type of hydrophobic, surgical grade rubber, plastic or silicone could be fashioned as grips 44A, 44B atop the gripping surface of pincers 26A, 26B. In at least one configuration of arm 14, pincers 26A, 26B are spaced apart in a generally parallel orientation relative to each another. In a preferred configuration, pincers 26A, 26B are angled away from each other. The offset portion 50A can include a mechanism (not shown) to control the degree of offset between pincers 26A, 26B. For example, one or both pincers 26A, 26B can be hingably mounted at the offset portion 50A with the degree of separation between them controlled by an adjustment screw or other incremental adjustment mechanism. Adjustments can result in the distal end of pincers 26A, 26B being spaced closer together or further apart, thereby increasing or decreasing the separation distance between jaws 38, 40 (best illustrated in FIGS. 17-18). The portion of pincers 26A, 26B attached to respective offset portion 50A can also, by actuation of an adjustment mechanism, such as an adjustment screw, be spaced closer together or further apart. Such adjustments can provide, for example, a greater distance between jaws 38, 40.

The pincers 26A, 26B, 28A, 28B are angled generally outwardly from planarity with the body of the forceps 10. The angle can be anywhere from 10-60 degrees, and preferably 20-45 degrees as illustrated pictorially in FIGS. 17-18. The separation distance between the distal end 16 of pincers 26A, 28A and 26B, 28B allows manipulation of tissues, nerves, fluids, and other possible vision-occluders to the extent that would not otherwise be possible with straight pincers or pincers with no separation distance between the distal end 16 of pincers 26A, 28A and 26B, 28B. Jaws 38, 40 are configured to hold at least a pair of fibrous swabs (e.g., fibrous swabs 62 shown in FIGS. 18-19), such as a plurality of cotton peanut sponges, cotton kittners or any like fibrous sponges/swabs. Examples of various contemplated fibrous swabs 62 and sponge pouch (e.g., see sponge pouch 60 in FIGS. 9-10) are commercially available for purchase from American Surgical Company. With the jaws 38, 40 of pincers 26A, 28A and 26B, 28B open, as pictorially illustrated in FIG. 17, at least a pair of fibrous swabs can simultaneously be secured between respective pincers 26A, 28A and 26B, 28B as shown in FIGS. 18-19. Articulating handles 22, 24 from an open position (see FIG. 17) toward a closed position (see FIGS. 18-19) closes jaws 38, 40 thereby grasping the pair of fibrous swabs 62 as shown. Grips 42A, 44A and 42B, 44B aid in grasping and retaining a grasp on the fibrous swabs 62 during manipulation of tissue, nerves, fluids or other bodily substances during, for example, a surgical procedure. Locking members, such as similar ones 34, 36 shown in FIGS. 1-10, can be configured on respective handles 22, 24 and aid in firmly securing fibrous swabs 62 within respective jaws 38, 40. Handles 22, 24 are articulated toward a closed position (see FIG. 18) to lock the fibrous swabs 62 within respective jaws 38, 40 of opposing pincers 26A, 28A and 26B, 28B as shown in FIGS. 18-19. As discussed above, adjusting the dimension and/or angle of offset portions 50A, 52A can alter the separation distance between the jaws 38, 40 holding the pair of fibrous swabs 62. For example, increasing the dimension/angle of offset portions 50A, 52A can increase the separation distance between opposing jaws 38, 40 and thereby the separation distance between the pair of fibrous swabs 62 grasped by the pair of opposing jaws 38, 40. Alterations or changes to the dimension and/or angle of pincers 26A, 28A and 26B, 28B can be accomplished as disclosed herein. It can be desirable to increase separation distance between the pair of opposing pincers 26A, 28A and 26B, 28B to increase, for example, the tissue separation during pushing and retracting tissue for creating enough tissue separation to prevent tissue from prolapsing while still providing a space through which the medical professional can see. Moreover, the angle of separation between pincers 26A, 28A and 26B, 28B allows further pushing and retraction of tissues, such as further manipulation of prolapsing tissue. Pincers 26A, 28A and 26B, 28B can both be angled upward or downward to further manipulate tissue, nerves, fluids, and other vision-occluders at a surgical site.

Figure 20:
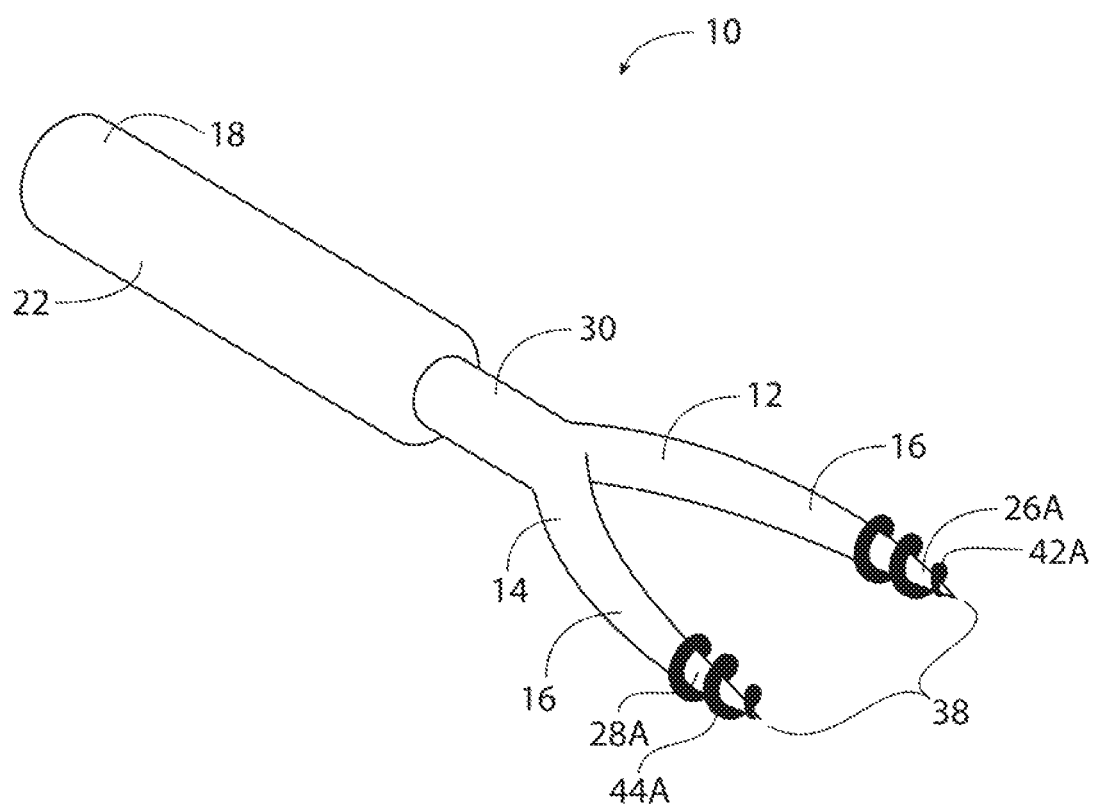
FIG. 20 is a perspective view of other forceps in accordance with an illustrative embodiment.
Figure 21:
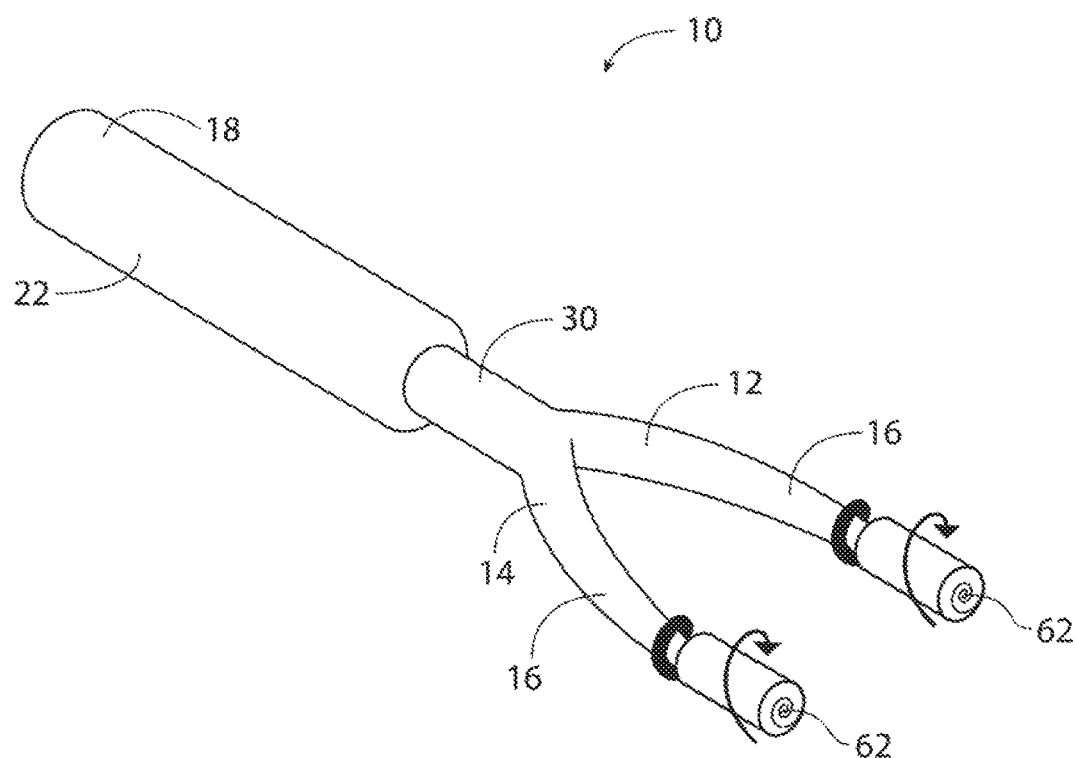
FIG. 21 is a perspective view of the forceps of FIG. 20 shown in a condition of use in accordance with an illustrative embodiment.

FIGS. 20-21 disclose forceps in accordance with another illustrative aspect of the present disclosure. The forceps 10 pictorially represented in FIGS. 20-21 include opposing arms 12, 14 that each extend generally between a distal end 16 and a proximal end 18 of the tool body or forceps 10. Pincer 26A is disposed at the distal end 16 of arm 12. Similarly, pincer 28A is disposed at the distal end of arm 14. In at least one preferred aspect of the present disclosure, pincers 26A, 28A are angled away from each other. Handle portion 22 is connected to arm 12, 14 at the proximal end 18. A shank portion 30 is disposed between the pincers and handle portion 22. The shank portion 30 can be lengthened or shortened to accommodate a desired tool body length. Arms 12, 14 are joined by the shank portion 30. The shank portion 30 can also be altered (e.g., lengthened) to offer more leverage at pincers 26A, 28A. The opposing arms 12, 14 are manipulated by manipulation of the handle portion 22.

As shown pictorially in FIGS. 20-21, arms 12, 14 are angled apart from shank portion 30 to separate pincers 26A, 28A to form jaw 38, or in this case the separation distance between pincers 26A, 28A.

As shown pictorially in FIGS. 20-21, arms 12, 14 include pincers 26A, 28A. Pincers 26A is attached to and offset from pincer 28A by shank portion 30. Pincers 26A. 28A can include grips 42A, 44A and grips 42A, 44A are preferably contoured to receive a round fibrous swab, as best shown in FIG. 21. Grips 42A, 44A can be configured from one or more protuberations, undulations, or irregularities in the material comprising the gripping surface. Grips 42A, 44A can be fashioned into the gripping surface of pincers 26A, 28A by making alterations to the surface of the material forming pincers 26A, 28A. In a preferred aspect of the present disclosure, arms 12, 14 are manufactured from a medical-grade alloy, such as surgical stainless steel. In another aspect, grips 42A, 44A are formed from a separate layer of material fashioned atop the gripping surface of pincers 26A, 28A. For example, any type of hydrophobic, surgical grade rubber, plastic or silicone could be fashioned as grips 42A, 44A atop the gripping surface of pincers 26A, 28A. In at least one configuration of arms 12, 14 pincers 26A, 28A are spaced apart in a generally parallel orientation relative to each another. In a preferred configuration, pincers 26A, 28A are angled away from each other. The shank 30 can include a mechanism (not shown) to control the degree of offset or in other words the separation distance between pincers 26A, 28A. For example, pincers 26A, 28A can be hingably mounted at shank 30 with the degree of separation between them controlled by an adjustment screw or other incremental adjustment mechanism. Adjustments can result in the distal end of pincers 26A, 28A being spaced closer together or further apart, thereby increasing or decreasing the separation distance of jaw 38. Such adjustments can provide, for example, a greater jaw 38 opening.

The pincers 26A, 28A are angled generally outwardly from each other in planarity with the body of the forceps 10. The angle can be anywhere from 10-60 degrees, and preferably 20-45 degrees as illustrated pictorially in FIGS. 20-21. The separation distance between the distal end 16 of pincers 26A, 28A allows manipulation of tissues, nerves, fluids, and other possible vision-occluders to the extent that would not otherwise be possible with no separation distance between the distal end 16 of pincers 26A, 28A. Jaw 38 is configured to hold at least a pair of fibrous swabs 62, such as a plurality of cotton peanut sponges, cotton kittners or any like fibrous sponges/swabs. Examples of various contemplated fibrous swabs 62 and sponge pouch (e.g., see sponge pouch 60 in FIGS. 9-10) are commercially available for purchase from American Surgical Company. At least a pair of fibrous swabs 62 can simultaneously be secured to respective pincers 26A, 28A as shown in FIG. 21. In one aspect, fibrous swabs 62 can be screwed, slide or pushed onto pincers 26A, 28A. Grips 42A, 44A aid in grasping and retaining a grasp on the fibrous swabs 62 during manipulation of tissue, nerves, fluids or other bodily substances during, for example, a surgical procedure. As discussed above, adjusting the dimension and/or angle of offset between pincers 26A, 28A can alter the separation distance between the pincers 26A, 28A or in other words the jaw 38 opening for holding the pair of fibrous swabs 62. For example, increasing the dimension/angle of pincers 26A, 28A at the shank portion 30 can increase the jaw 38 opening and thereby the separation distance between the pair of fibrous swabs 62 grasped by the pair of opposing pincers 26A, 28A. Alterations or changes to the dimension and/or angle of pincers 26A, 28A can be accomplished as disclosed herein. It can be desirable to increase separation distance between the pair of opposing pincers 26A, 28A to increase, for example, the tissue separation during pushing and retracting tissue for creating enough tissue separation to prevent tissue from prolapsing while still providing a space through which the medical professional can see. Moreover, the angle of separation between pincers 26A, 28A allows further pushing and retraction of tissues, such as further manipulation of prolapsing tissue. Pincers 26A, 28A can both be angled upward or downward our of planarity with the body of the forceps 10 to further manipulate tissue, nerves, fluids, and other vision-occluders at a surgical site.

FIGS. 22-23 disclose forceps in accordance with another illustrative aspect of the present disclosure. The forceps 10 pictorially represented in FIGS. 22-23 include opposing arms 12, 14 that each extend generally between a distal end 16 and a proximal end 18 of the tool body or forceps 10. A fibrous swab 62 is disposed at the distal end 16 of arms 12, 14. In at least one preferred aspect of the present disclosure, arms 12, 14 are angled away from each other. Handle portion 22 is connected to arms 12, 14 at the proximal end 18. A shank portion is disposed between the arms 12, 14 and handle portion 22. The shank portion can be lengthened or shortened to accommodate a desired tool body length. Arms 12, 14 are joined together by the shank portion of handle portion 22. The shank portion can also be altered (e.g., lengthened) to offer more leverage on arms 12, 14 and respective fibrous swabs 62. The opposing arms 12, 14 are manipulated by manipulation of the handle portion 22.

As shown pictorially in FIGS. 22-23, arms 12, 14 are angled apart from the shank portion of handle portion 22 to separate the arms 12, 14 and respective fibrous swabs 62 to form jaw 38, or in this case the separation distance between respective fibrous swabs 26A, 28A.

As shown pictorially in FIGS. 22-23, arms 12, 14 include arms terminating in fibrous swabs 62. Arms 12, 14 can include grips 42A, 44A in a way similarly shown in FIGS. 20-21 and grips 42A, 44A are preferably contoured to receive a round fibrous swab, as best shown in FIG. 21. The grips can be configured from one or more protuberances, undulations, or irregularities in the material comprising the gripping surface. Grips can be fashioned into the gripping surface at the distal end 16 of arms 12, 14 by making alterations to the surface of the material forming pincers the distal end 16 of arms 12, 14. In one aspect of the present disclosure, arms 12, 14 are manufactured from a medical-grade alloy, such as surgical stainless steel. In another aspect, grips fashioned similar to grips 42A, 44A in FIGS. 20-21 are formed from a separate layer of material fashioned atop the gripping surface. For example, any type of hydrophobic, surgical grade rubber, plastic or silicone could be fashioned as grips. In another aspect of the present disclosure, forceps 10 are manufactured from a surgical grade disposable material to include arms 12, 14 terminating in a pair of fibrous swaps 62, whereby after use the entire forceps 10 is discarded.

In at least one configuration of arms 12, 14 are spaced apart in a generally parallel orientation relative to each another. In a preferred configuration, arms 12, 14 are angled away from each other. The shank portion of handle portion 22 can include a mechanism (not shown) to control the degree of offset or in other words the separation distance between arms 12, 14, fibrous swabs 62, and thereby the jaw 38 opening. For example, arms 12, 14 can be hingably mounted at the shank portion of handle portion 22 with the degree of separation between them controlled by an adjustment screw or other incremental adjustment mechanism. Adjustments can result in the distal end of arms 12, 14 being spaced closer together or further apart, thereby increasing or decreasing the separation distance of jaw 38. Such adjustments can provide, for example, a greater jaw 38 opening.

The arms 12, 14 are angled generally outwardly from each other in planarity with the body of the forceps 10. The angle can be anywhere from 10-60 degrees, and preferably 20-35 degrees as illustrated pictorially in FIG. 22. The separation distance between the distal end 16 of arms 12, 14 and thereby respective fibrous swabs 62 allows manipulation of tissues, nerves, fluids, and other possible vision-occluders to the extent that would not otherwise be possible with no separation distance between arms 12, 14. Jaw 38 is configured to hold at least a pair of fibrous swabs 62, such as a plurality of cotton peanut sponges, cotton kittners or any like fibrous sponges/swabs. Examples of various contemplated fibrous swabs 62 and sponge pouch (e.g., see sponge pouch 60 in FIGS. 9-10) are commercially available for purchase from American Surgical Company. At least a pair of fibrous swabs 62 can simultaneously be secured as shown in FIGS. 22-23. In one aspect, fibrous swabs 62 can be screwed, slide or pushed onto the ends of arms 12, 14. In another aspect, the end of arms 12, 14 are manufactured to already include a pair of fibrous swabs 62 whereby the forceps 10 are disposable and discarded after use. Grips fashioned in a like manner as grips 42A, 44A shown in FIGS. 20-21 can aid in grasping and retaining a grasp on the fibrous swabs 62 during manipulation of tissue, nerves, fluids or other bodily substances during, for example, a surgical procedure. As discussed above, adjusting the dimension and/or angle of offset between arms 12, 14, and particularly respective fibrous swabs 62, can alter the separation distance between the swabs or in other words the jaw 38 opening for holding the pair of fibrous swabs 62. Alterations or changes to the dimension and/or angle of arms 12, 14 can be accomplished as disclosed herein. It can be desirable to increase separation distance between the pair of opposing fibrous swabs 62 to increase, for example, the tissue separation during pushing and retracting tissue for creating enough tissue separation to prevent tissue from prolapsing while still providing a space through which the medical professional can see. Moreover, the angle of separation between swabs 62 allows further pushing and retraction of tissues, such as further manipulation of prolapsing tissue. As best shown in FIG. 23, arms 12, 14 can both be angled upward or downward our of planarity with the body of the forceps 10 to further manipulate tissue, nerves, fluids, and other vision-occluders at a surgical site.

The disclosure is not to be limited to the particular embodiments described herein. In particular, the disclosure contemplates numerous variations in the type of ways in which embodiments of the disclosure can be applied to metering systems with variable blend and variable application rate controls for particulate matter. The foregoing description has been presented for purposes of illustration and description. It is not intended to be an exhaustive list or limit any of the disclosure to the precise forms disclosed. It is contemplated that other alternatives or exemplary aspects that are considered included in the disclosure. The description is merely examples of embodiments, processes or methods of the disclosure. It is understood that any other modifications, substitutions, and/or additions can be made, which are within the intended spirit and scope of the disclosure. For the foregoing, it can be seen that the disclosure accomplishes at least all of the intended objectives.

The previous detailed description is of a small number of embodiments for implementing the disclosure and is not intended to be limiting in scope. The following claims set forth a number of the embodiments of the disclosure disclosed with greater particularity.

What is claimed is:

1. A handheld forceps for grasping and simultaneously holding multiple objects, the forceps comprising:
   a first opposing arm having proximal and distal ends;
   a second opposing arm having proximal and distal ends;
   a hinge connecting the first opposing arm and the second opposing arm together between the proximal and distal ends, wherein the first opposing arm and the second opposing arm articulate relative to each other about the hinge;
   handle portions comprising:
      a first handle portion at the proximal end of the first opposing arm, the first handle portion having an open and closed position for articulating the distal end of the first opposing arm open and closed;
      a second handle portion at the proximal end of the second opposing arm, the second handle portion having an open and closed position for articulating the distal end of the second opposing arm open and closed;
   at least a first pincer with grips and a second pincer with grips at the distal end of each of the first opposing arm and the second opposing arm;
   a first jaw comprising the first pincer at the distal end of the first opposing arm and the first pincer at the distal end of the second opposing arm; and
   a second jaw comprising the second pincer at the distal end of the first opposing arm and the second pincer at the distal end of the second opposing arm;
   wherein the grip of the first pincer at the distal end of the first opposing arm faces the grip of the second pincer at the distal end of the second opposing arm;
   wherein the grip of the second pincer at the distal end of the first opposing arm faces the grip of the first pincer at the distal end of the second opposing arm;
      wherein the first pincer at the distal end of the first opposing arm, the first pincer at the distal end of the second opposing arm, the second pincer at the distal end of the first opposing arm, and the second pincer at the distal end of the second opposing arm are stacked in alignment with each other such that, in a closed position, the grip of the first pincer at the distal end of the first opposing arm abuts the grip of the first pincer at the distal end of the second opposing arm along substantially the entire length of both grips and the grip of the second pincer at the distal end of the first opposing arm abuts the grip of the second pincer at the distal end of the second opposing arm along substantially the entire length of both grips.

2. The handheld forceps of claim 1 wherein the first jaw and the second jaw are both closed in the closed position of the handle portions.

3. The handheld forceps of claim 1 wherein the first jaw and the second jaw are both open in the open position of the handle portions.

4. The handheld forceps of claim 1 wherein the first jaw and the second jaw are longitudinally aligned.

5. The handheld forceps of claim 1 wherein a pair of inner pincers comprise the first pincer at the distal end of the first opposing arm and the second pincer at the distal end of the second opposing arm.

6. The handheld forceps of claim 1 wherein a pair of outer pincers comprise the second pincer at the distal end of the first opposing arm and the first pincer at the distal end of the second opposing arm.

7. The handheld forceps of claim 1 further comprising a locking mechanism between the proximal ends and the hinge, wherein the locking mechanism comprises a first locking member on the first opposing arm and a second locking member of the second opposing arm, wherein the first and second locking members include teeth.

8. A handheld medical tool, comprising:
   a first opposing arm having proximal and distal ends;
   a second opposing arm having proximal and distal ends;
   a hinge connecting the first opposing arm and the second opposing arm together between the proximal and distal ends, wherein the first opposing arm and the second opposing arm articulate relative to each other about the hinge;
   handle portions comprising:
      a first handle portion at the proximal end of the first opposing arm;
      a second handle portion at the proximal end of the second opposing arm;
      wherein the first and second handle portion have an open and closed position for articulating the distal end of the first and second opposing arm open and closed;
   a first pincer with a first grip at the distal end of the first opposing arm and a first pincer with a first grip at the distal end of the second opposing arm;
   a second pincer with a second grip at the distal end of the first opposing arm and a second pincer with a second grip at the distal end of the second opposing arm; and
   a pair of pincers comprising the second pincer at the distal end of the first opposing arm and the first pincer at the distal end of the second opposing arm disposed between the first pincer at the distal end of the first opposing arm and the second pincer at the distal end of the second opposing arm
   wherein the first grip at the distal end of the first opposing arm faces the first grip at the distal end of the second opposing arm and the second grip at the distal end of the second opposing arm faces the second grip of the first opposing arm;
   wherein each of the second pincers at the distal ends of the first and the second opposing arms are in alignment with each of the first pincers at the distal ends of the first and second opposing arms such that, in a closed position, the grip of the first pincer at the distal end of the first opposing arm abuts the grip of the first pincer at the distal end of the second opposing arm along substantially the entire length of both grips and the grip of the second pincer at the distal end of the first opposing arm abuts the grip of the second pincer at the distal end of the second opposing arm along substantially the entire length of both grips.

9. The handheld medical tool of claim 8 wherein the pair of pincers articulate about the hinge independently.

10. The handheld medical tool of claim 8 wherein the first opposing arm includes the first pincer at the distal end of the first opposing arm and the second pincer at the distal end of the first opposing arm.

11. The handheld medical tool of claim 8 wherein the first and second pincers at the distal end of the first opposing arm articulate independent of the first pincer at the distal end of the second opposing arm.

12. The handheld medical tool of claim 8 wherein the first and second pincers at the distal end of the first opposing arm articulate together.

13. The handheld medical tool of claim 8 further comprising a locking mechanism between the proximal ends and the hinge, wherein the locking mechanism comprises a first locking member on the first opposing arm and a second locking member of the second opposing arm, wherein the first and second locking member include teeth.

14. A handheld medical instrument comprising:
first and second opposing arms having proximal and distal ends;
a hinge connecting the opposing arms together between the proximal and distal ends, wherein the opposing arms articulate relative to each other about the hinge;
handle portions comprising:
  a first handle portion at the proximal end of the first opposing arm, the first handle portion having an open and closed position for articulating the distal end of the first opposing arm open and closed;
  a second handle portion at the proximal end of the second opposing arm, the second handle portion having an open and closed position for articulating the distal end of the second opposing arm open and closed;
a first pincer with a first grip at the distal end of the first opposing arm and a first pincer with a first grip at the distal end of the second opposing arm; and
a second pincer with a second grip at the distal end of the first opposing arm and a second pincer with a second grip at the distal end of the second opposing arm;
wherein the first grip at the distal end of the first opposing arm faces the first and second grips at the distal end of the second opposing arm;
wherein the second grip at the distal end of the second opposing arm faces the first and second grips at the distal end of the first opposing arm;
wherein in a closed position, the grip of the first pincer at the distal end of the first opposing arm abuts the grip of the first pincer at the distal end of the second opposing arm along substantially the entire length of both grips and the grip of the second pincer at the distal end of the first opposing arm abuts the grip of the second pincer at the distal end of the second opposing arm along substantially the entire length of both grips.

15. The handheld medical instrument of claim 14 wherein the first pincer at the distal end of the second opposing arm is disposed between the first pincer at the distal end of the first opposing arm and the second pincer at the distal end of the first opposing arm when the first and second opposing arms are both open and closed.

16. The handheld medical instrument of claim 14 wherein the pair of jaws articulate together simultaneously.

17. The handheld medical instrument of claim 14 wherein the pair of jaws have an open and closed position, wherein the pair of jaws are in the open position with the handle portions in the open position.

18. The handheld medical instrument of claim 14 wherein the pair of jaws are oriented longitudinally relative to the hinge.

19. The handheld medical instrument of claim 14 wherein the pincers comprise needle nose pincers.

* * * * *